(12) United States Patent
Levesque et al.

(10) Patent No.: US 8,740,847 B2
(45) Date of Patent: Jun. 3, 2014

(54) FLUID DELIVERY DEVICE NEEDLE RETRACTION MECHANISMS, CARTRIDGES AND EXPANDABLE HYDRAULIC FLUID SEALS

(75) Inventors: Steven F. Levesque, North Pembroke, MA (US); Geoffrey H. Jenkins, Wayland, MA (US); Robert L. Standley, Acton, MA (US); Matthew P. Johnson, Boylston, MA (US); Daniel A. Dube, Jr., Putnam, CT (US)

(73) Assignee: Valeritas, Inc., Bridgewater, NJ (US)

( * ) Notice: Subject to any disclaimer, the term of this patent is extended or adjusted under 35 U.S.C. 154(b) by 287 days.

(21) Appl. No.: 13/156,839

(22) Filed: Jun. 9, 2011

(65) Prior Publication Data

US 2011/0306929 A1    Dec. 15, 2011

Related U.S. Application Data

(60) Provisional application No. 61/353,004, filed on Jun. 9, 2010.

(51) Int. Cl.
  *A61M 37/00*    (2006.01)
  *A61M 5/00*    (2006.01)

(52) U.S. Cl.
  USPC .......................................... 604/150; 604/244

(58) Field of Classification Search
  USPC ....................................................... 604/150
  See application file for complete search history.

(56) References Cited

U.S. PATENT DOCUMENTS

| | | | |
|---|---|---|---|
| 4,443,218 A | 4/1984 | DeCant, Jr. et al. | |
| 5,041,094 A | 8/1991 | Perego et al. | |
| 5,165,869 A | 11/1992 | Reynolds | |
| 5,298,023 A * | 3/1994 | Haber et al. | 604/90 |
| 5,492,534 A | 2/1996 | Athayde et al. | |
| 5,716,343 A | 2/1998 | Kriesel et al. | |
| 5,976,109 A | 11/1999 | Heruth | |
| 6,416,495 B1 | 7/2002 | Kriesel et al. | |
| 6,629,954 B1 | 10/2003 | Heruth | |
| 6,824,529 B2 | 11/2004 | Gross et al. | |
| 6,902,207 B2 | 6/2005 | Lickliter | |

(Continued)

FOREIGN PATENT DOCUMENTS

| | | |
|---|---|---|
| DE | 3634725 | 4/1988 |
| WO | 9626751 | 9/1996 |

(Continued)

OTHER PUBLICATIONS

International Search Report and Written Opinion for PCT/US2011/039771 dated Oct. 4, 2011.

(Continued)

*Primary Examiner* — Jason Flick
(74) *Attorney, Agent, or Firm* — Morgan, Lewis & Bockius LLP

(57) ABSTRACT

A fluid delivery device includes an automatic needle retraction mechanism configured to automatically retract a delivery end of a needle into a housing. In one embodiment, the needle assembly is configured to automatically withdraw the delivery end of the needle into the housing upon an actuator moving from the first position to the second position. In one embodiment, the needle assembly is configured to automatically withdraw the delivery end of the needle into the housing upon decoupling a bottom surface of the housing from a skin surface.

30 Claims, 20 Drawing Sheets

(56) References Cited

U.S. PATENT DOCUMENTS

| | | | |
|---|---|---|---|
| 7,481,792 B2* | 1/2009 | Gonnelli et al. | 604/142 |
| 7,530,964 B2 | 5/2009 | Lavi et al. | |
| 7,530,968 B2 | 5/2009 | Gonnelli | |
| 2007/0233001 A1* | 10/2007 | Burroughs et al. | 604/131 |
| 2008/0051701 A1 | 2/2008 | Kriesel | |
| 2008/0083789 A1* | 4/2008 | Brugner | 222/386 |
| 2009/0240232 A1* | 9/2009 | Gonnelli et al. | 604/506 |
| 2010/0331773 A1* | 12/2010 | Frederiksen et al. | 604/84 |

FOREIGN PATENT DOCUMENTS

| | | |
|---|---|---|
| WO | 2009065932 | 5/2009 |
| WO | 2009144546 | 12/2009 |
| WO | 2011046950 | 4/2011 |

OTHER PUBLICATIONS

Office Action for U.S. Appl. No. 12/336,395 dated Sep. 21, 2011.

* cited by examiner

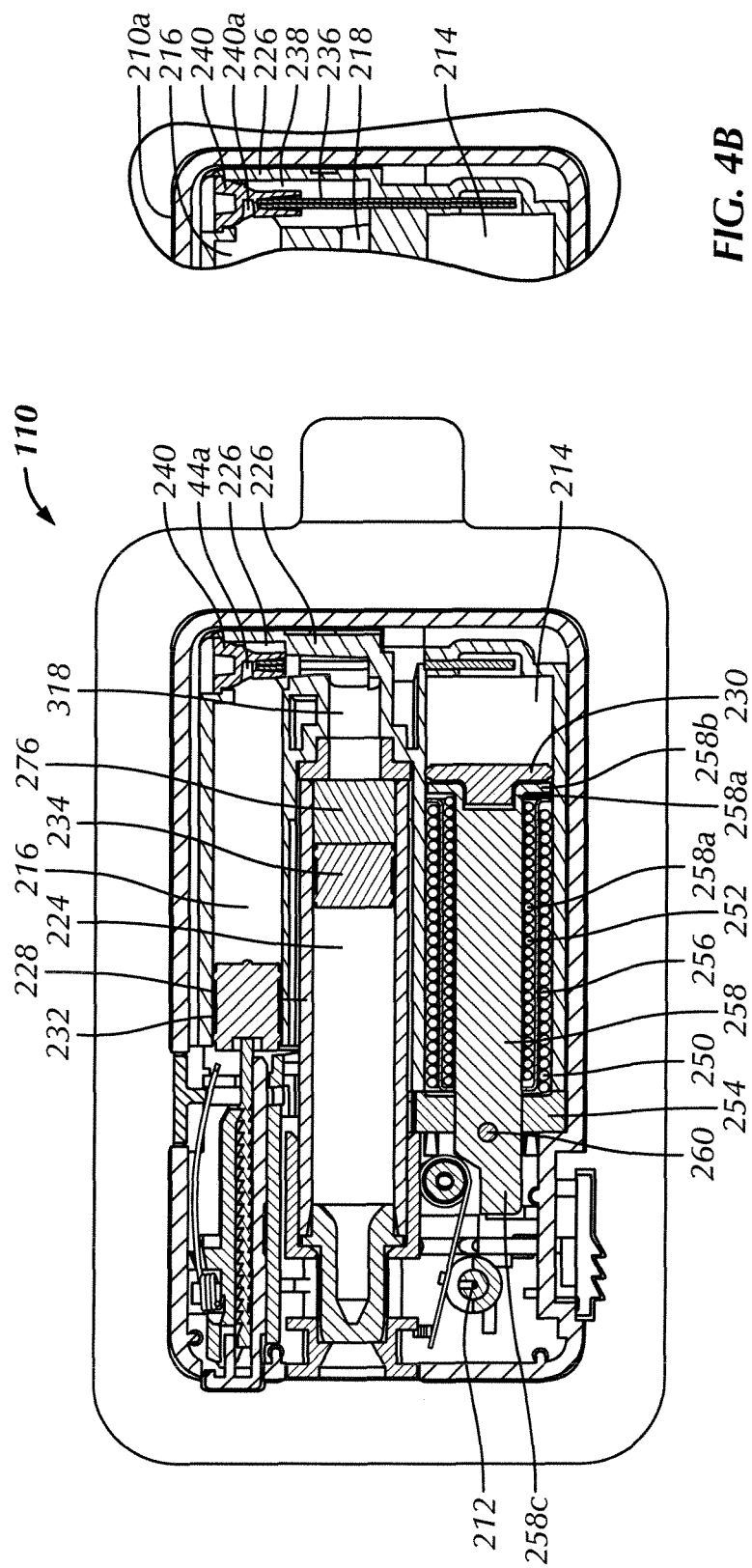

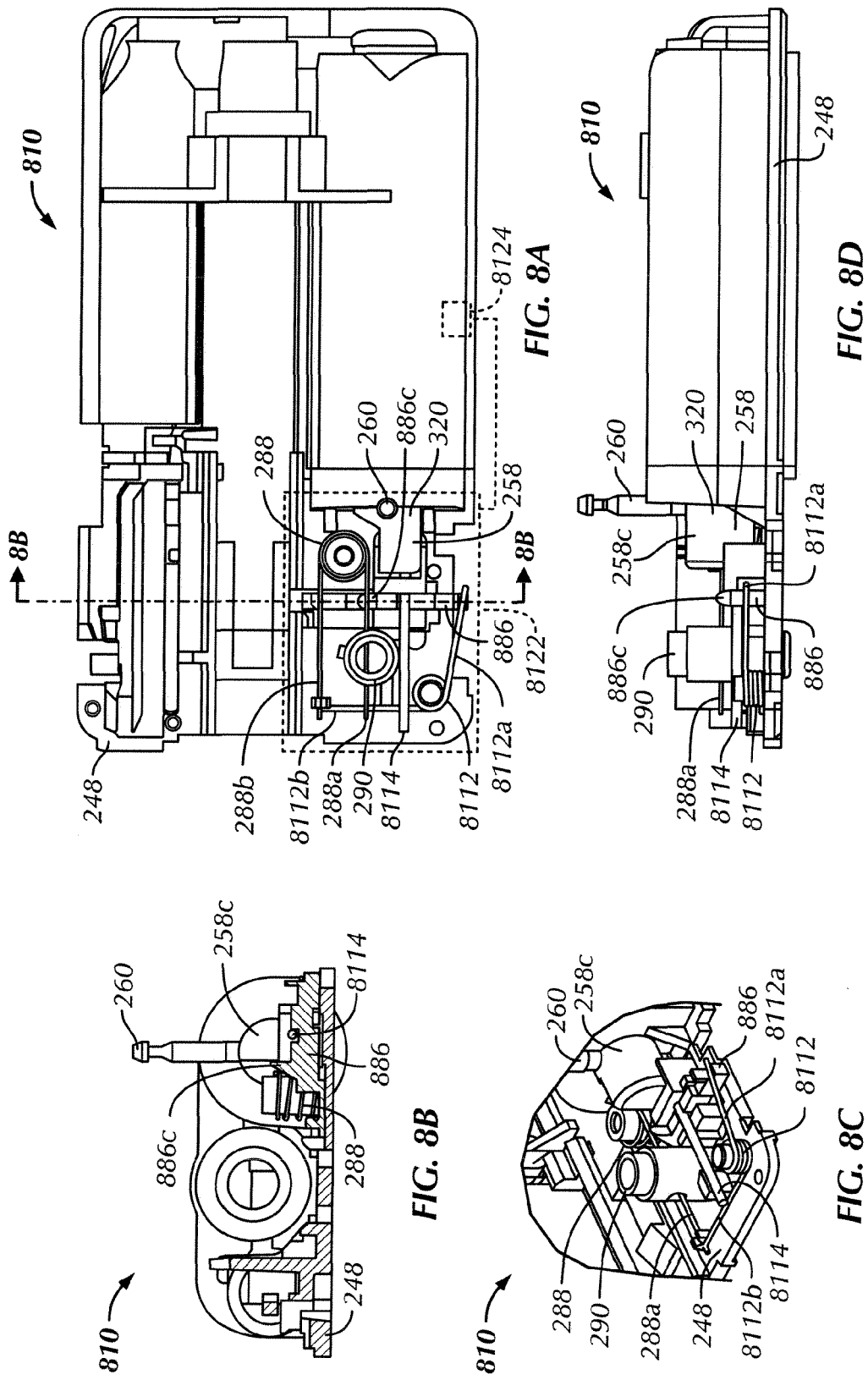

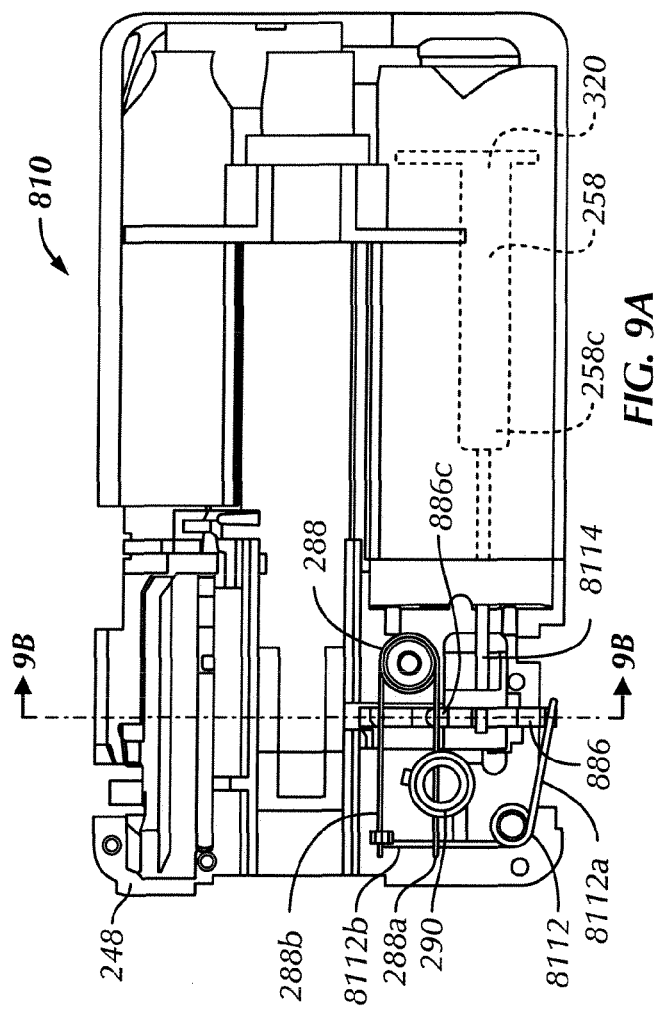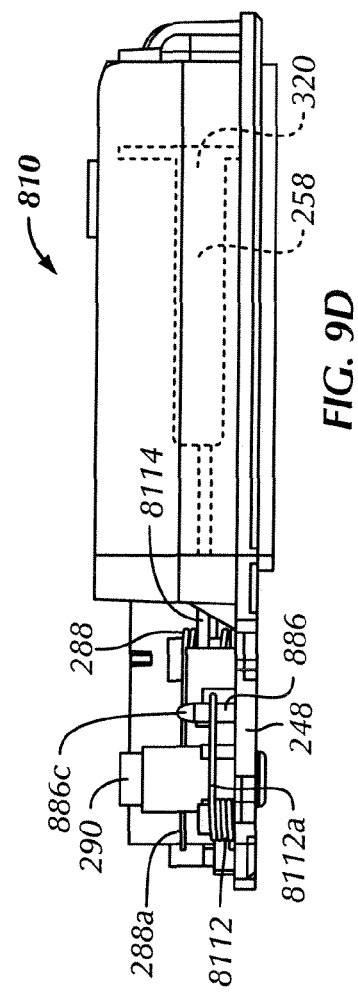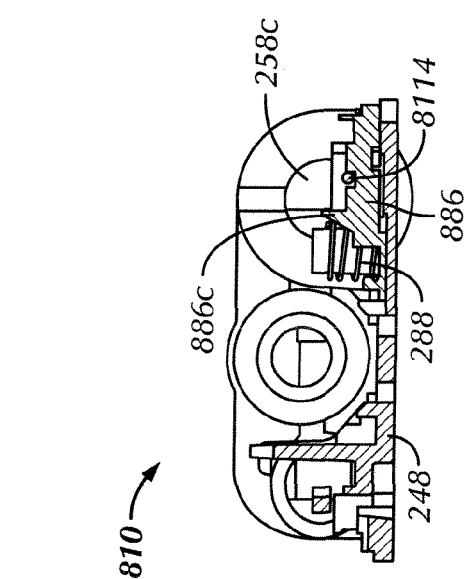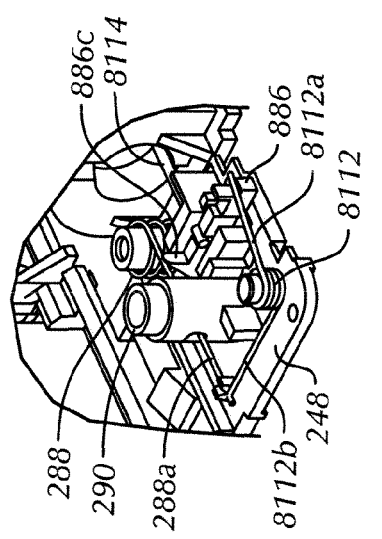

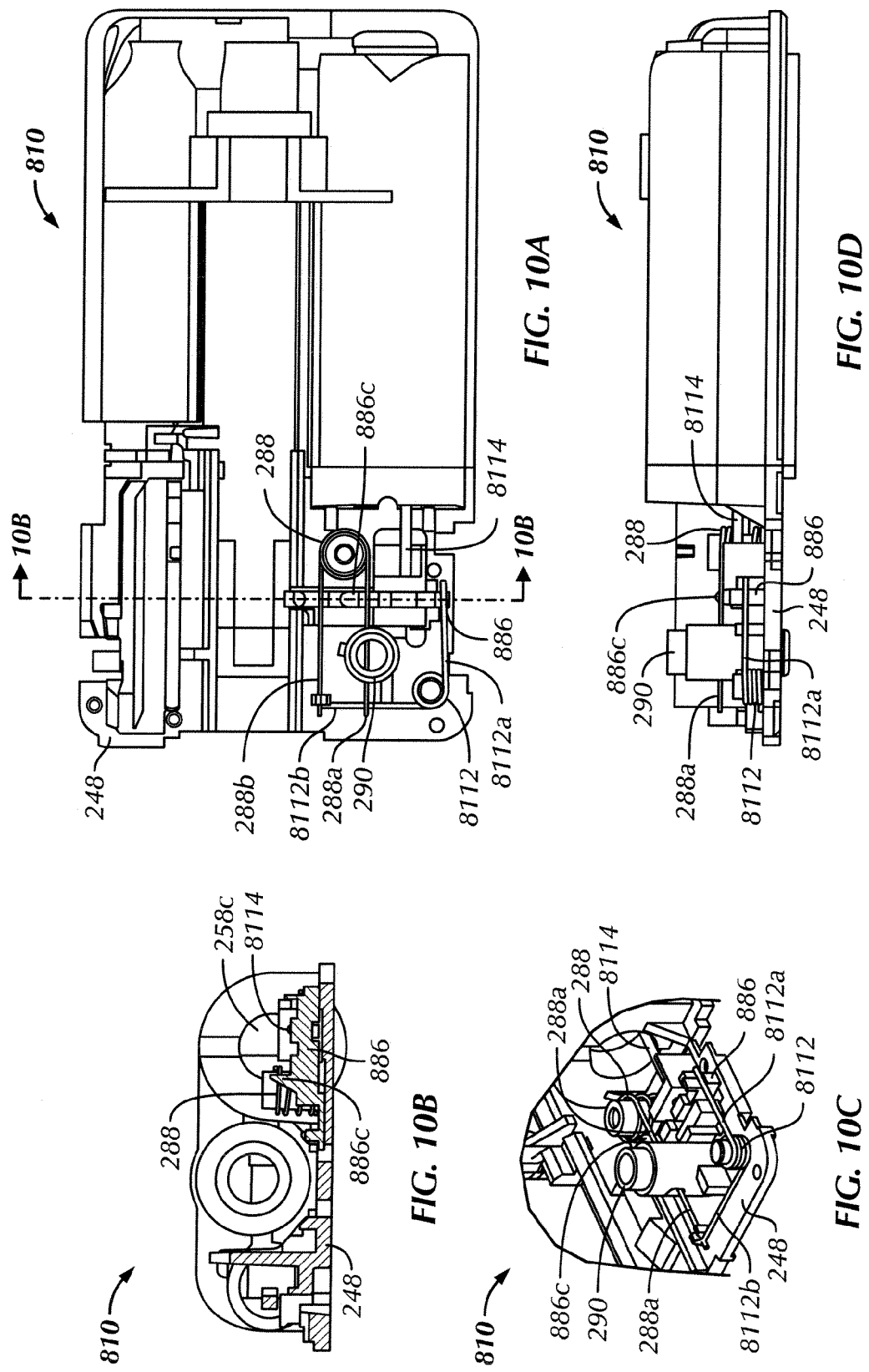

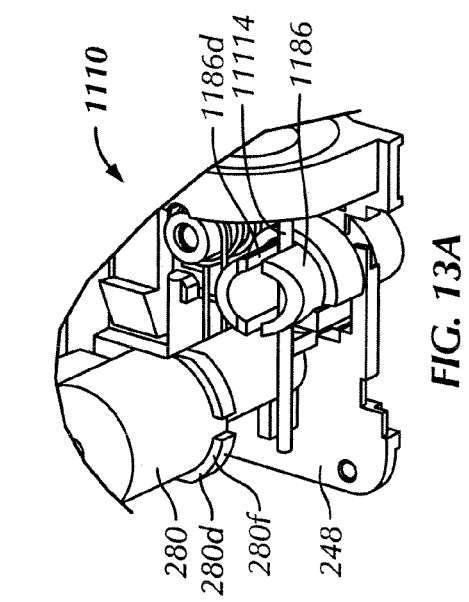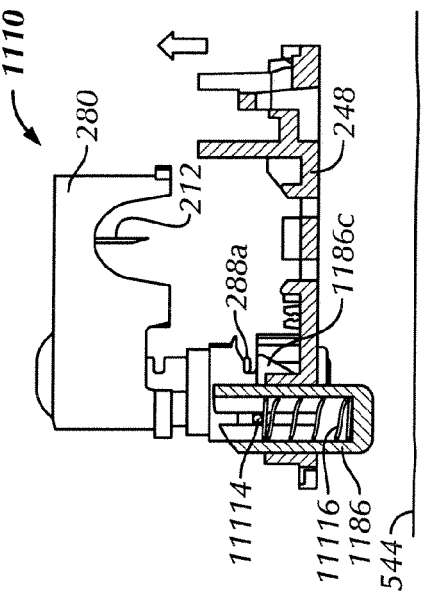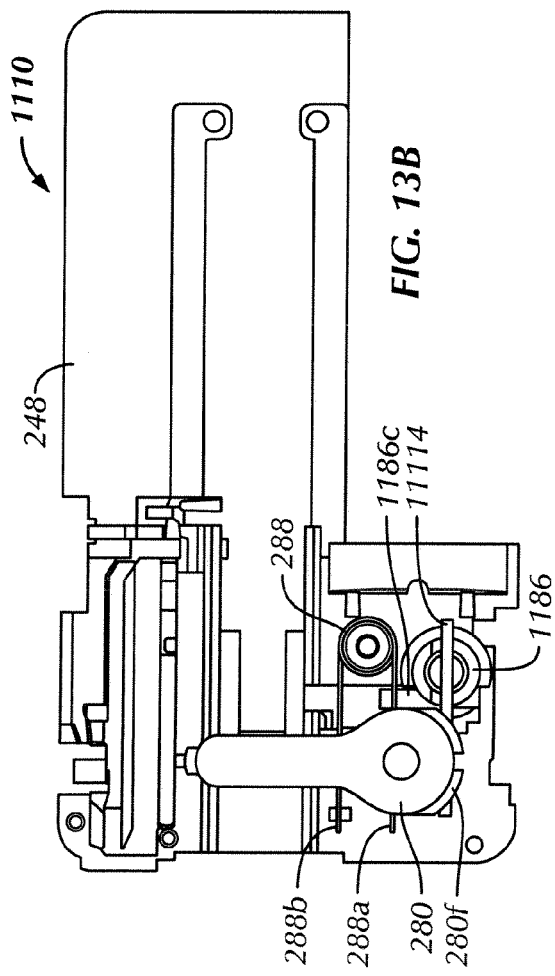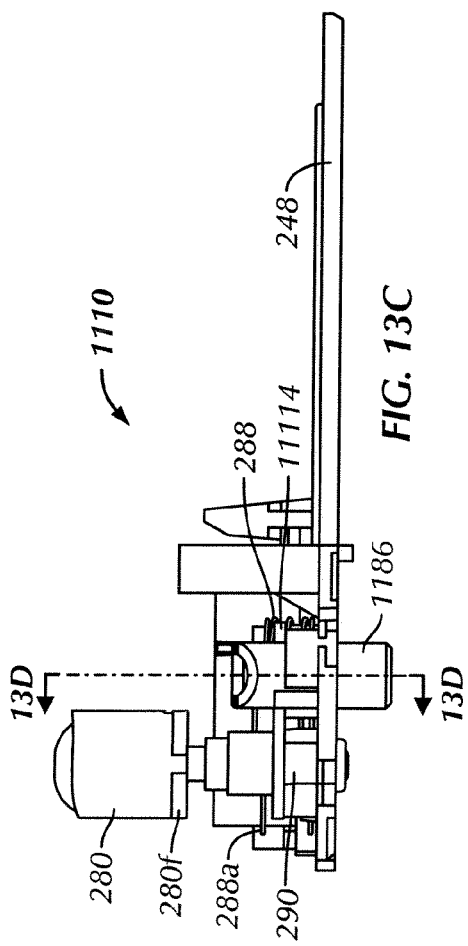

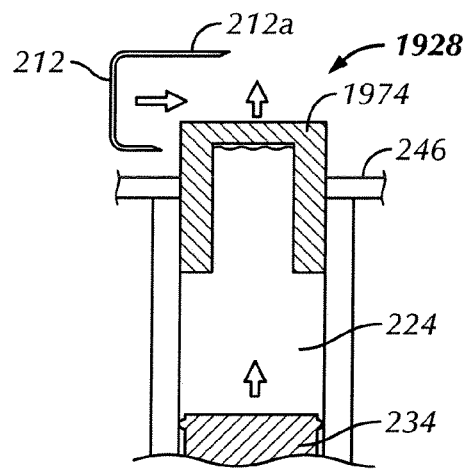
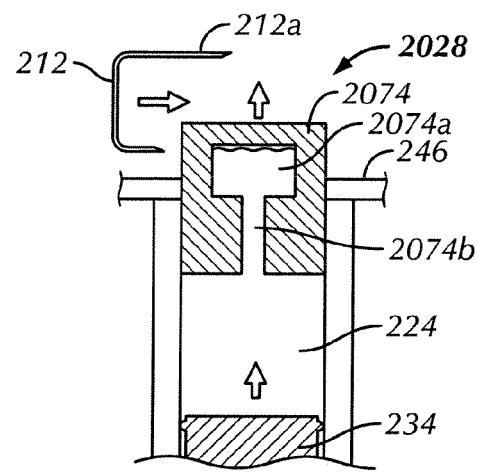
*FIG. 19*    *FIG. 20*
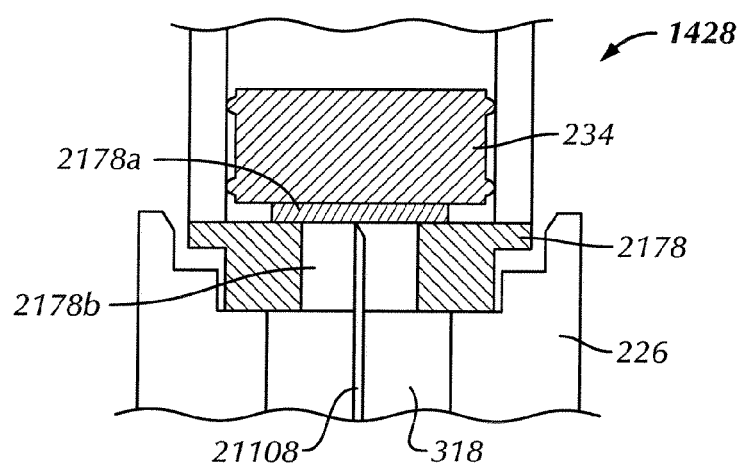
*FIG. 21*

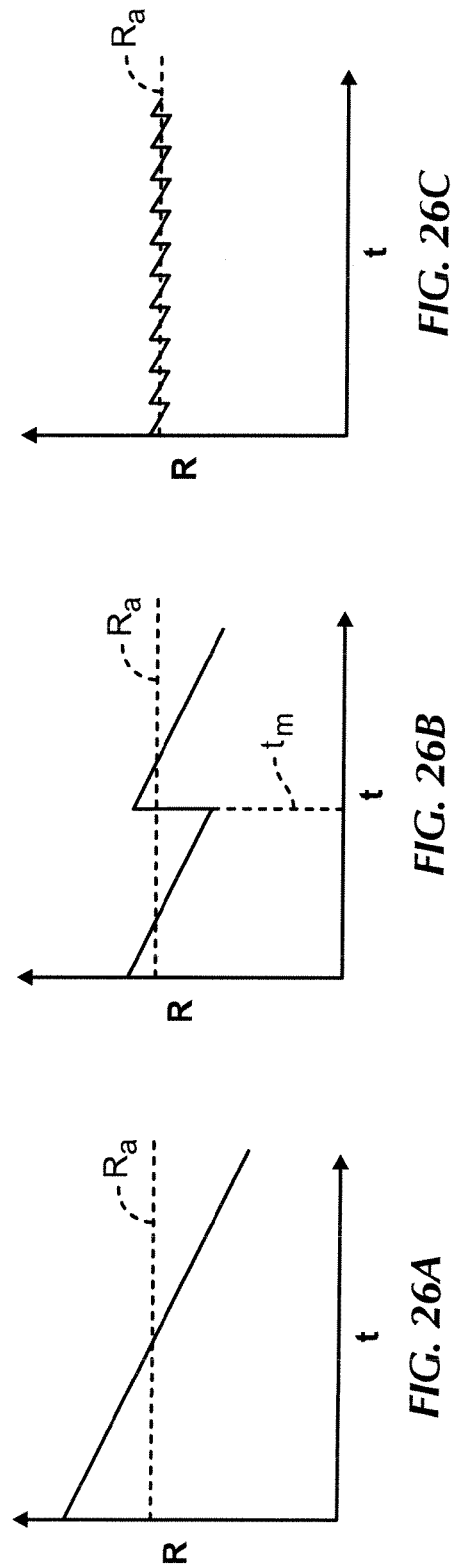
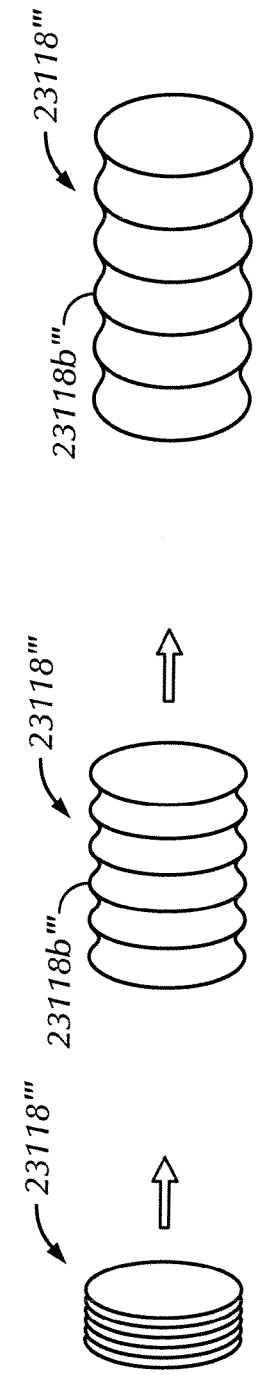

FLUID DELIVERY DEVICE NEEDLE RETRACTION MECHANISMS, CARTRIDGES AND EXPANDABLE HYDRAULIC FLUID SEALS

CROSS-REFERENCE TO RELATED APPLICATIONS

This application claims the benefit of U.S. Provisional Patent Application No. 61/353,004 filed Jun. 9, 2010 entitled "Fluid Delivery Device Cartridges, Needle Retraction Mechanisms and Expandable Hydraulic Fluid Seals", incorporated by reference herein in its entirety.

BACKGROUND OF THE INVENTION

The present invention generally relates to a fluid delivery device and more particularly to fluid delivery device needle retraction mechanisms, cartridges and expandable hydraulic fluid seals for use with an ambulatory device for delivering a medicament to a patient.

Many attempts have been made to provide continuous or near continuous dosing of drugs and other fluids, such as insulin, using pump systems. Although some systems for continuous delivery work quite well, individuals using these systems, particularly in continuous dose mode, need to monitor the devices closely to ensure continuity and accuracy of dosing under variable environmental conditions such as temperature and air pressure. In addition, there are few options for individuals who require the ability to vary the dose of medication quickly and accurately, and most of the available options are cumbersome, difficult to operate, intrusive, and/or expensive.

Accordingly, it would be desirable to provide a simple, intuitive, inexpensive ambulatory device able to provide fluid dosing under patient control, as well as safety and consistency in the metered or continuous dose over a wide range of environmental conditions.

BRIEF SUMMARY OF THE INVENTION

In one embodiment there is a fluid delivery device that comprises (a) a housing configured to be coupled to a skin surface in an engaged position, (b) a fluid reservoir coupled to the housing, (c) an actuator coupled to the housing and configured to deliver a force to the fluid reservoir, the actuator having a first position and a second position, and (c) a needle assembly having a needle the needle having a delivery end configured to extend from the housing and into the skin surface in a delivery configuration, the needle assembly being configured to automatically withdraw the delivery end of the needle into the housing upon the actuator moving from the first position to the second position. In a further embodiment, the fluid delivery device comprises a locking member configured to keep the delivery end of the needle within the housing in a locked position.

In a further embodiment, the fluid delivery device comprises a needle release configured to position the locking member into the locked position upon the actuator moving from the first position into the second position. In one embodiment, the needle release is spring biased toward the locking member in the first position. In one embodiment, the needle release includes at least one projection configured to engage with the locking member. In one embodiment, the at least one projection is ramped.

In a further embodiment, the fluid delivery device comprises an actuation button coupled to the needle and having a sleeve surrounding at least a portion of the needle, wherein the locking member is spring biased toward the sleeve, the sleeve having at least one abutment surface configured to engage with the locking member to prevent at least one of engaging and disengaging the needle. In one embodiment, the at least one abutment surface includes a first abutment surface and a second abutment surface, the locking member engageable with the first abutment surface to releaseably retain the needle in the engaged position, the locking member engageable with the second abutment surface to unreleaseably retain the needle in the locked position. In one embodiment, the first abutment surface is axially spaced along the needle from the second abutment surface and the actuation button is configured to be spring biased away from the skin surface in the delivery configuration.

In one embodiment, the needle release is spring biased, the needle release being retained in the first position by a lock released coupled to the actuator, the lock release configured to release the needle release and allow the needle release to move in a direction of the spring bias in the second position. In one embodiment, the lock release includes a shaft extending from the actuator. In one embodiment, the locking member comprises a helical torsion spring. In one embodiment, the locking member is configured to releaseably retain the needle in the engaged position.

In a further embodiment, the fluid delivery device comprises a first hydraulic chamber, a second hydraulic chamber, and a flow restrictor fluidly coupling the first hydraulic chamber and a second hydraulic chamber, wherein the actuator is configured to deliver the force to the fluid reservoir through the first and second hydraulic chambers. In one embodiment, the actuator reaches an end of travel in the second position. In one embodiment, fluid is delivered through the needle in the first position and the fluid ceases to be delivered from the needle in the second position. In one embodiment, the housing includes a bottom surface, the bottom surface including an adhesive configured to releaseably couple the housing to the skin surface in the engaged position.

In another embodiment, a fluid delivery device comprises (a) a housing having a bottom surface, the bottom surface including an adhesive configured to releaseably couple the housing to a skin surface in an engaged position, (b) a needle assembly having a needle, the needle having a delivery end configured to extend from the housing and into the skin surface in a delivery configuration, the needle assembly being configured to automatically withdraw the delivery end of the needle into the housing upon decoupling the bottom surface of the housing from the skin surface. In a further embodiment, the fluid delivery device comprises a locking member configured to keep the delivery end of the needle within the housing in a locked position. In a further embodiment, the fluid delivery device comprises a needle release configured to position the locking member into the locked position upon decoupling the housing from the skin surface. In one embodiment, the needle release includes at least one projection configured to engage with the locking member. In one embodiment, the at least one projection is ramped. In one embodiment, the needle release is spring biased toward the skin surface in the engaged position. In a further embodiment, the fluid delivery device comprises a lock release configured to compress a spring biasing the needle release in the engaged position, the spring configured to move the needle release upon decoupling the housing from the skin surface. In one embodiment, the needle release is contained within the housing in the engaged position and extends from the housing in the locked position.

In a further embodiment, the fluid delivery device comprises an actuation button coupled to the needle and having a sleeve surrounding at least a portion of the needle, wherein the locking member is spring biased toward the sleeve, the sleeve having at least one abutment surface configured to engaging with the locking member to prevent at least one of engaging and disengaging the needle. In one embodiment, the at least one abutment surface includes a first abutment surface and a second abutment surface, the locking member engageable with the first abutment surface to releaseably retain the needle in the engaged position, the locking member engageable with the second abutment surface to unreleaseably retain the needle in the locked position. In one embodiment, the first abutment surface is axially spaced along the needle from the second abutment surface and the actuation button is configured to be spring biased away from the skin surface in the delivery configuration. In one embodiment, the locking member comprises a helical torsion spring. In one embodiment, the locking member is configured to releaseably retain the needle in the engaged position. In a further embodiment, the fluid delivery device comprises a fluid reservoir coupled to the housing, and an actuator coupled to the housing and configured to deliver a force to the fluid reservoir. In a further embodiment, the fluid delivery device comprises a first hydraulic chamber, a second hydraulic chamber, and a flow restrictor fluidly coupling the first hydraulic chamber and a second hydraulic chamber, wherein the actuator is configured to deliver a force to the fluid reservoir through the first and second hydraulic chambers. In one embodiment, the actuator includes a first position and a second position, and wherein the needle assembly is configured to automatically withdraw the delivery end of the needle into the housing upon the actuator moving from the first position to the second position.

In another embodiment, a fluid delivery device comprises (a) a housing having a first hydraulic chamber and a second hydraulic chamber, (b) a flow restrictor fluidly coupling the first hydraulic chamber and the second hydraulic chamber, (c) a cartridge having a container forming a fluid reservoir sealed at a proximal end with a piston, the cartridge being insertable into the housing and configured to couple the piston with the second hydraulic chamber, the fluid reservoir being substantially filled with a liquid prior to inserting the cartridge within the housing, the cartridge including a septum configured to be pierced by a delivery needle, and (d) an actuator coupled to the housing and configured to deliver a force to the piston through the first and second hydraulic chambers. In a further embodiment, the fluid delivery device comprises a cartridge seal coupled between the proximal end of the cartridge and the housing when the cartridge is inserted into the housing. In one embodiment, the cartridge seal is compressible.

In a further embodiment, the fluid delivery device comprises a hydraulic cap extending through the cartridge seal and coupling the piston and the second hydraulic chamber. In one embodiment, the hydraulic cap is substantially rigid. In one embodiment, the proximal end of the cartridge includes an overflow channel in fluid communication with the second hydraulic chamber when the cartridge is inserted into the housing. In one embodiment, the overflow channel is formed between an outer peripheral edge of the proximal end of the cartridge and an inner peripheral edge of the proximal end of the cartridge, the outer peripheral edge extending axially further from the cartridge than the inner peripheral edge.

In one embodiment, the cartridge seal covers the second hydraulic reservoir prior to inserting the cartridge into the housing and the second hydraulic reservoir includes a piercing member configured to pierce the cartridge seal upon insertion of the cartridge into the housing. In one embodiment, the piercing member includes a needle. In one embodiment, the septum is slidably coupled with the container. In one embodiment, the septum is configured to slide distally with respect to the container upon inserting the cartridge into the housing. In one embodiment, the septum includes a space for receiving an end of the delivery needle and a fluid passageway fluidly coupling the space and the fluid reservoir, the fluid passageway having a cross sectional area that is less than a cross sectional area of the space. In one embodiment, the septum seals a distal end of the container. In one embodiment, the septum is displaced with respect to the container when the septum is displaced upon inserting the cartridge into the housing. In one embodiment, the cartridge includes a volume and a pressure, the volume being reduceable to enable insertion of the cartridge into the housing prior to engagement with the delivery needle and without changing the pressure.

In one embodiment, the second hydraulic chamber is configured to expel hydraulic fluid upon insertion of the cartridge into the housing. In one embodiment, the cartridge further comprises a relief valve, the piston configured to expel air and/or fluid through the relief valve upon insertion of the cartridge into the housing. In one embodiment, the cartridge further comprises a relief piston configured to slide distally upon insertion of the cartridge into the housing. In one embodiment, the cartridge further comprises a septum configured to be pierced by the delivery needle. In a further embodiment, the fluid delivery device comprises a cap coupling the piston and the second hydraulic reservoir when the cartridge is inserted into the housing, the cap having a side wall and at least one of a top surface or a bottom surface that extends axially outwardly from the side wall, at least one of the top surface or the bottom surface being configured to invert upon inserting the cartridge into the housing.

In another embodiment, a cartridge for use with a fluid delivery device comprises a container forming a fluid reservoir having a volume, a pressure and a septum configured to be pierced by a delivery needle, the volume being reduceable to enable insertion of the cartridge into the fluid delivery device prior to engagement with a delivery needle and without changing the pressure of the fluid reservoir. In one embodiment, the septum is slideably coupled with the container. In one embodiment, the septum is configured to slide distally with respect to the container upon inserting the cartridge with the fluid delivery device. In one embodiment, the septum includes a space for receiving an end of the delivery needle and a fluid passageway fluidly coupling the space and the fluid reservoir. In one embodiment, the septum seals a distal end of the container and a piston seals a proximal end of the container. In one embodiment, the septum is displaced with respect to the container when a piston within the container is displaced upon inserting the cartridge into the fluid delivery device. In one embodiment, the fluid delivery device comprises a piston slideable within the container. In one embodiment, the container is substantially rigid. In one embodiment, the fluid delivery device comprises a relief valve and a piston, the piston configured to expel air and/or fluid through the relief valve upon insertion of the cartridge into the fluid delivery device. In one embodiment, the fluid delivery device comprises a relief piston configured to slide distally upon insertion of the cartridge into the fluid delivery device.

In another embodiment, a fluid delivery device comprises (a) a housing having a first hydraulic chamber and a second hydraulic chamber, (b) a flow restrictor fluidly coupling the first hydraulic chamber and a second hydraulic chamber, (c) a cartridge forming a fluid reservoir between a slideable piston and a stopper, the stopper configured to seal a distal end of the cartridge after the fluid reservoir is substantially filled with a liquid, the piston being coupled with the second hydraulic chamber, (c) an actuator coupled to the housing and configured to deliver a force to the piston through the first and second hydraulic chambers. In one embodiment, the cartridge includes a septum configured to receive a delivery needle.

In another embodiment, a fluid delivery device comprises (a) a housing having a first hydraulic chamber and a second hydraulic chamber, (b) a flow restrictor fluidly coupling the first hydraulic chamber and a second hydraulic chamber, (c) a fluid reservoir, (d) a seal sealing the second hydraulic chamber and configured to couple with the fluid reservoir, the seal being expandable between a compressed position and an expanded position, and (e) an actuator coupled to the first hydraulic chamber and configured to expand the seal and deliver a force to the fluid reservoir through the first and second hydraulic chambers.

In one embodiment, the cross sectional area of a distal end of the seal is smaller than the cross sectional area of a proximal end of the seal in the expanded position. In one embodiment, the seal includes at least two telescoping members. In one embodiment, the seal includes at least two cylindrical members having different diameters. In one embodiment, the seal is generally conically shaped in the expanded position. In one embodiment, the fluid delivery device comprises a cartridge having a container, a slideable piston and the fluid reservoir.

BRIEF DESCRIPTION OF THE SEVERAL VIEWS OF THE DRAWINGS

The foregoing summary, as well as the following detailed description of embodiments of the fluid delivery device will be better understood when read in conjunction with the appended drawings of exemplary embodiments. It should be understood, however, that the invention is not limited to the precise arrangements and instrumentalities shown.

In the drawings:

FIG. 4A is a top cross sectional view of the fluid delivery device shown in FIG. 1 taken along line 4A-4A of FIG. 1;

FIG. 4B is a top partial cross sectional view of the fluid delivery device shown in FIG. 1 taken along a length of a flow restrictor;

FIGS. 8A-8D are various partial views of a fluid delivery device in accordance with an exemplary embodiment of the present invention in an initial position;

FIGS. 9A-9D are various partial views of the fluid delivery device shown in FIGS. 8A-8D in a delivery position;

FIGS. 10A-10D are various partial views of the fluid delivery device shown in FIGS. 8A-8D in a locked out or completed delivery position;

FIGS. 13A-13D are various partial views of the fluid delivery device shown in FIGS. 11A-11D in a locked out or disengaged position;

FIG. 19 is a cross sectional view of a cartridge for use with a fluid delivery device similar to the fluid delivery device shown in FIG. 1 in accordance with an exemplary embodiment of the present invention;

FIG. 20 is a cross sectional view of a cartridge for use with a fluid delivery device similar to the fluid delivery device shown in FIG. 1 in accordance with an exemplary embodiment of the present invention;

FIG. 21 is a cross sectional view of a cartridge for use with a fluid delivery device similar to the fluid delivery device shown in FIG. 1 in accordance with an exemplary embodiment of the present invention;

FIGS. 26A-26C are graphs of the delivery rate R versus time t of exemplary fluid delivery devices without a hydraulic fluid seal, with a two stage hydraulic fluid seal and a multistage hydraulic fluid seal respectively; and FIGS. 27A-27C are perspective views of another exemplary embodiment of the hydraulic fluid seal in the initial, midway and completed positions respectively.

DETAILED DESCRIPTION OF THE INVENTION

Figure 1:
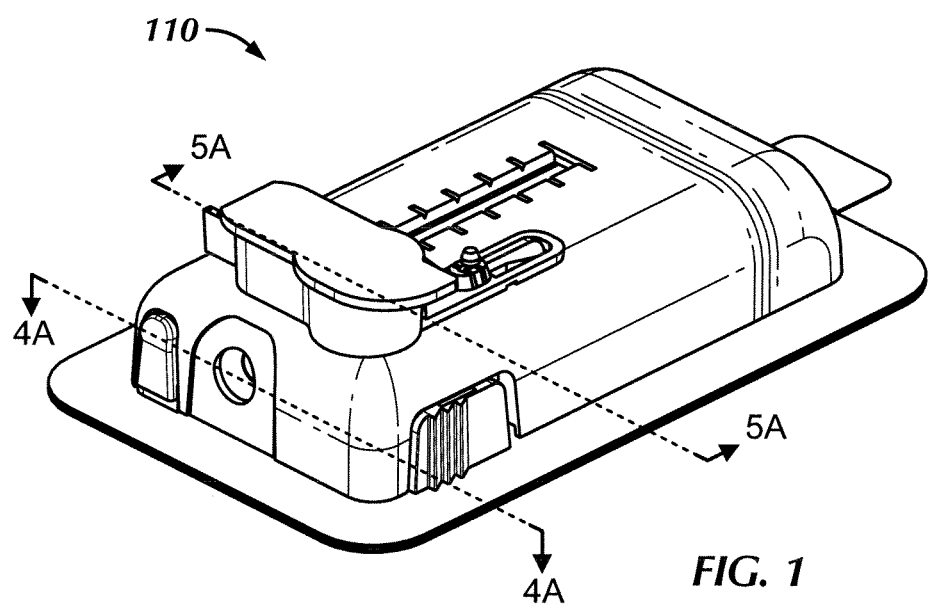
FIG. 1 is a perspective view a fluid delivery device in accordance with an exemplary embodiment of the present invention.

Referring to the drawings in detail, wherein like reference numerals indicate like elements throughout, there is shown in FIGS. 1-7B a fluid delivery device, generally designated 110, in accordance with an exemplary embodiment of the present invention. Fluid delivery device 110 may include one or more features described herein which facilitate or improve accurate delivery of a fluid and ease of use by a user or patient. The benefits provided by these features translate readily to improved patient compliance and improved therapeutic outcome.

In one embodiment, fluid delivery device 110 is a discrete ambulatory insulin delivery pump. Fluid delivery device 110 may be single use, disposable and incapable of reuse. In preferred embodiments, fluid delivery device 110 is completely mechanical and hydraulic and has no electronic components or aspects. Fluid delivery device 110 may provide excellent therapeutic capability in a small, single use, disposable package and can be produced using high volume manufacturing fabrication (e.g., injection molding) and assembly processes, allowing for low cost-of goods. Devices of the invention can be used for a broad range of applications, including, but not limited to, clinical applications (administration of medicaments, etc.) and biomedical research (e.g., microinjection into cells, nuclear or organelle transplantation, isolation of single cells or hybridomas, etc.).

In one embodiment, fluid delivery device 110 is a device for dispensing, delivering, or administering the fluid or agent to the user or patient. The fluid may be a low viscosity gel agent and or a therapeutic agent. In one embodiment, the fluid is an analgesic agent. In one embodiment, the fluid is insulin. In one embodiment, the fluid is a U100 insulin. In another embodiment the fluid is a U200 insulin. In another embodiment the fluid is a U300 insulin. In another embodiment, the fluid is a U500 insulin. In another embodiment the fluid is any insulin between U100 and U500. In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using fluid delivery device 110. As used herein "patients" or "user" can be human or non-human animals; the use of fluid delivery device 110 is not confined solely to human medicine, but can be equally applied to veterinarian medicine.

Fluid delivery device 110 may dispense the fluid over a sustained period of time (i.e., basal delivery). In one embodiment, the fluid delivery rate is continuously or near continuously delivered to the user over the sustained period of time. Fluid delivery device 110 may also be capable of dispensing a supplementary amount of fluid, in addition to the basal amount, on demand, under patient control (i.e., bolus delivery). In one embodiment, as discussed further below, the bolus amount delivered in a single, selectable administration is pre-determined. In preferred embodiments, fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Figure 3:
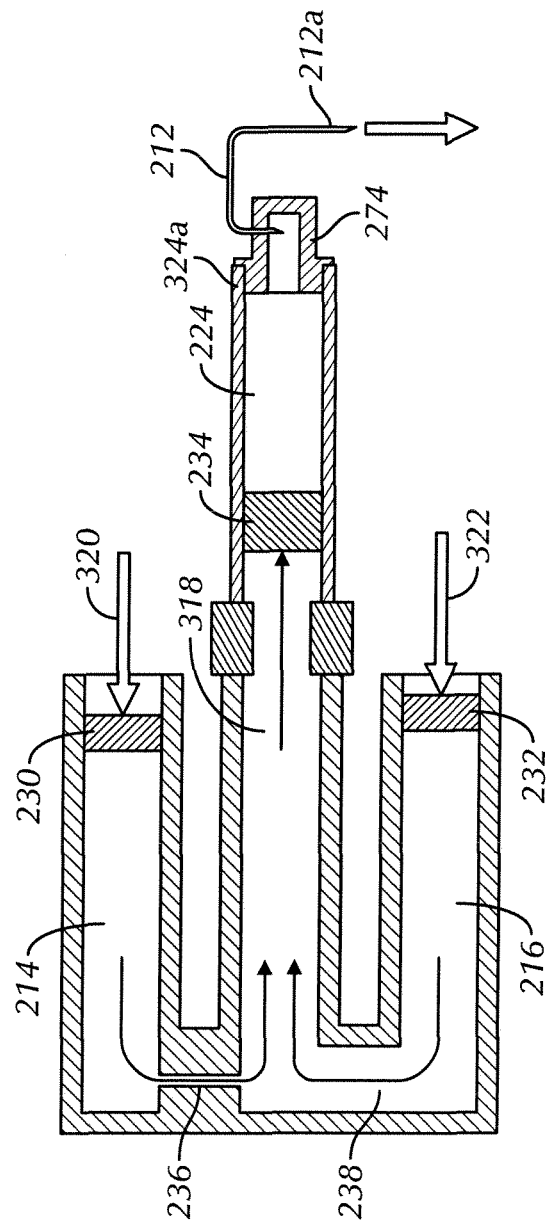
FIG. 3 is a schematic top, cross sectional view of a fluid delivery device in accordance with an exemplary embodiment of the present invention.

One exemplary embodiment of fluid delivery device 110 is shown in the schematic of FIG. 3, illustrating select components and their relationships. Fluid delivery device 110 may have a first operable state for dispensing or delivering the fluid through an infusion set or needle 212 at a continuous or sustained basal dosage and a second operable state for delivering the fluid through needle 212 at a bolus dosage. In some embodiments, fluid delivery device 110 can be in both the first and second operable states concurrently, i.e., delivering a bolus dose in addition to a basal dose of fluid. In one embodiment, the bolus dosage is a fixed incremental dosage. In another embodiment, the bolus function is capable of delivering multiple discrete bolus increments when activated by the user. In certain embodiments, the basal rate of delivery is predetermined and preset.

Referring to FIGS. 3 and 4A, in one embodiment, fluid delivery device 110 contains three hydraulic reservoirs or chambers, a hydraulic basal chamber 214, a hydraulic bolus reservoir 216 and a hydraulic pump chamber 318. In some embodiments, hydraulic bolus chamber 214 shares a common chamber with hydraulic pump chamber 318 and/or the flow between hydraulic bolus chamber 216 and hydraulic pump chamber 318 is unrestricted as described further herein. In a preferred embodiment, hydraulic basal and bolus chambers 214, 216 are separately and independently actuated by separate and independent basal and bolus actuators 320, 322.

Referring to FIG. 3, in one embodiment, hydraulic basal and bolus chambers 214, 216 act on hydraulic pump chamber 318 which in turn acts on a fluid reservoir or delivery chamber 224, containing the fluid. In other embodiments, hydraulic basal and bolus chambers 214, 216 each act on a distinct pump chamber and each pump chamber is functionally connected to a separate fluid reservoir (not shown).

Figure 2:
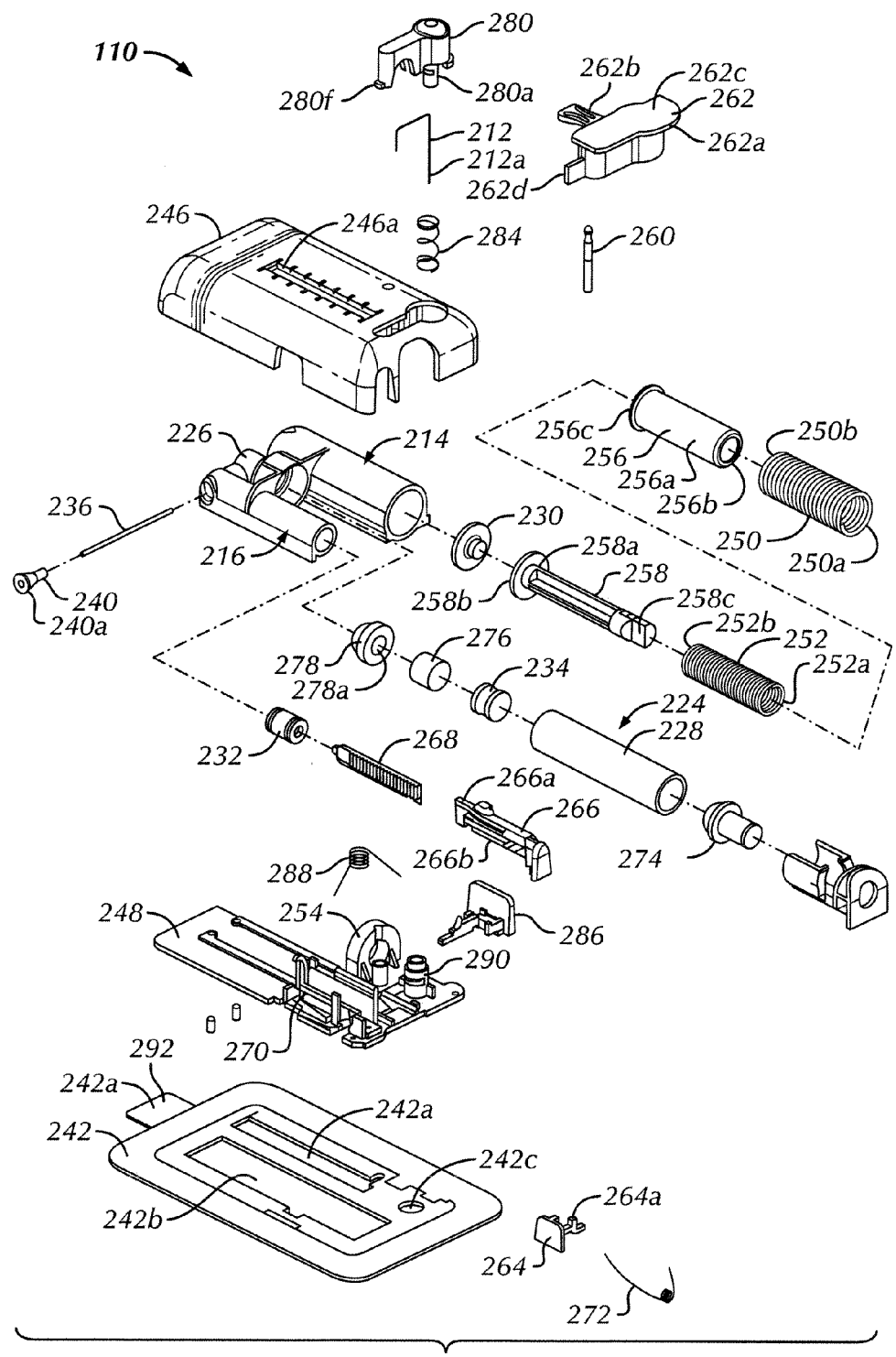
FIG. 2 is an exploded perspective view of the fluid delivery device shown in FIG. 1.

Referring to FIGS. 2 and 3, hydraulic basal, bolus and pump chambers 214, 216, 318 may be defined by a manifold 226. In one embodiment, manifold 226 is an integral one piece component. In one embodiment, manifold 226 is comprised of a polymer. In one embodiment, manifold 226 is comprised of acrylonitrile butadiene styrene (ABS). In one embodiment, manifold 226 is comprised of polyvinyl chloride (PVC). In one embodiment, fluid reservoir 224 and a portion of hydraulic pump chamber 318 are defined by a fluid cartridge 228. In one embodiment, fluid cartridge 228 is comprised of a polymer. In one embodiment, fluid cartridge 228 is comprised of Topas 6017 S-04. In one embodiment, fluid cartridge 228 is comprised of glass. Hydraulic basal, bolus and pump chambers 214, 216, 318 and fluid reservoir 224 may be cylindrical. In other embodiments, hydraulic pump chambers 214, 216, 318 and fluid reservoir 224 have any cross sectional shape such as square, rectangular or triangular. In one embodiment, a first moveable barrier 230 separates basal actuator 320 and hydraulic basal chamber 214. In one embodiment, a second moveable barrier 232 separates bolus actuator 322 and hydraulic bolus chamber 216. In one embodiment, a third moveable barrier 234 separates hydraulic pump chamber 318 and fluid reservoir 224. First, second and third moveable barriers 230, 232, 234 may be pistons as described further below. In other embodiments, first, second and third moveable barriers 230, 232, 234 are any barriers that can transfer movement between two chambers such as membranes or expandable walls.

Hydraulic basal and bolus chambers 214, 216 may be parallel, spaced on either side of and generally aligned with hydraulic pump chamber 318 and fluid reservoir 224 as illustrated in order to provide a more compact configuration. In one embodiment, hydraulic pump chamber 318 is provided toward one side of fluid delivery device 110. In other embodiments, hydraulic basal, bolus and pump chambers 214, 216, 318 are arranged in any configuration that allows fluid communication and achieves the desired outer shape of fluid delivery device 110 such as stacked in a triangle configuration.

Basal actuator 320 may act on hydraulic basal chamber 214 containing a hydraulic fluid to pressurize hydraulic basal chamber 214 and force a hydraulic fluid through a flow restrictor 236 into hydraulic pump chamber 318. Generally, but not necessarily, the hydraulic fluid in hydraulic pump chamber 318 may be identical or similar in composition to the hydraulic fluid in hydraulic basal chamber 214. Actuation of basal actuator 320 may result in a flow of hydraulic fluid from hydraulic basal reservoir 320 into hydraulic pump chamber 318 at a reduced rate as compared to if flow restrictor 236 was not provided. As the volume of hydraulic fluid in hydraulic pump chamber 318 increases, third moveable barrier 234 is displaced, compressing or reducing the volume of fluid reservoir 224 and causing the fluid contained therein to be expelled through an output orifice or needle 212 at a sustained basal rate. In one embodiment, the basal rate is substantially constant.

In some embodiments, a bolus actuator 322 independently acts on hydraulic bolus chamber 216. In one embodiment, bolus actuator 322 acts directly on hydraulic pump chamber 318. It should be understood, however, that the invention is not limited to devices comprising both a basal and a bolus capability. Devices of the invention having one or more features described herein may comprise a basal capability, a bolus capability, or both basal and bolus capabilities.

Both hydraulic bolus chamber 216 and hydraulic pump chamber 318 may contain hydraulic fluid of an appropriate viscosity. Generally, but not necessarily, the composition of the hydraulic fluid in hydraulic pump chamber 318 will be identical or similar to the composition of the hydraulic fluid in hydraulic basal and bolus chambers 214, 216. Actuation or displacement of bolus actuator 322 independently displaces third moveable barrier 234, compressing or reducing the volume of fluid reservoir 224 and causing the fluid contained therein to be expelled through an output orifice such as needle 212. Concurrent operation of both basal and bolus actuators 320, 322 causes compression of fluid reservoir 224 by an amount greater than operation of either actuator alone.

When present, both basal and bolus actuators 320, 322 may be integrated within the hydraulically actuated system in a manner that allows each function to provide independent displacement force onto a common movable barrier 234, which in turn displaces fluid from within a common fluid reservoir 224 to dispense the fluid from fluid delivery device 110. In other embodiments, basal and bolus actuators 320, 322 may be integrated within the hydraulically actuated system in a manner that allows each function to provide independent displacement force onto separate moveable barriers (not shown), which in turn displace fluid from within separate fluid reservoirs (not shown). Examples of a multi-cartridge fluid delivery devices for use with the inventions presented herein is disclosed in U.S. Patent Application Publication No. 2009/0240232 which is hereby incorporated by reference in its entirety.

In one embodiment, fluid delivery device 110 utilizes a combination of force, high, very high or ultra high viscosity fluid, and flow restriction to deliver the fluid on a continuous or sustained basis. Flow restrictor 236 may facilitate continuous delivery of fluid at a basal rate by, among other aspects, creating a large pressure differential or pressure drop between hydraulic basal chamber 214 and hydraulic pump chamber 318, allowing the system to tolerate a wider range of frictional variations in the system such as movement of third movable barrier 234 within fluid cartridge 228, tolerate small changes in the resistance to flow, and overcome potential occlusions in the flow path. In one embodiment, the pressure differential between hydraulic basal chamber 214 and hydraulic pump chamber 318 during use is approximately 10:1. In one embodiment, the pressure differential between hydraulic basal chamber 214 and hydraulic pump chamber 318 during use is approximately 46:1. In one embodiment, hydraulic basal chamber 214 operates at approximately 46.8 psi. In one embodiment, hydraulic pump chamber 318 operates at approximately 0.5 psi to approximately 5 psi.

Flow restrictor 236 is dimensionally adapted to control the rate of fluid flow therethrough. In one embodiment, flow restrictor 236 has a diameter of approximately 1-1000 µm. It should be understood that all ranges provided herein encompass both the beginning and end points of the range (e.g., includes 1 and 1000 µm in a range of from about 1 to about 1000 µm), as well as all values in between. Whatever the shape of flow restrictor 236, the cross sectional area and the length of the opening will be sized to achieve the flow rate desired. For example, flow restrictor 236 may be about one-ten thousandths of an inch (or 2-3 µm) in diameter. Depending on use, flow restrictor 236 size can be anything, including but not limited to an opening between 200 nm-500 nm, or 500 nm-1000 nm, or 1-2 µm, or 5-10 µm, or 10-1000 µm. In one embodiment, the outer diameter of flow restrictor 236 is approximately 0.026 inches and the inner diameter of flow restrictor 236 is one of approximately 0.00758 inches, 0.00708 inches and 0.00638 inches. In one embodiment, the length and outer diameter of flow restrictor 236 remains constant from device to device based on the size of manifold 226 and the inner diameter of flow restrictor 236 may be altered to achieve the desired flow rate. Other sizes and dimensions of flow restrictor 236 can be selected, and the size and dimension selected will depend upon the application at hand and, in particular, the viscosity of the hydraulic fluid and the force applied by basal actuator 320. In one embodiment, flow restrictor 236 is comprised of glass. Having a flow restrictor 236 comprised of glass may help to ensure that flow restrictor 236 has a substantially accurate and constant cross sectional size and shape. Those of skill in the art will understand that any suitable flow restrictor 236 may be employed, and that the size and the shape of flow restrictor 236 can vary to achieve the desired flow rate of the fluid being mediated under the expected conditions, including temperature and ambient pressure. Flow restrictor 236 need not be circular in cross sectional shape, and can be an oval, a square, a rectangle, a triangle, a polygon, or irregular in shape. The size and shape of flow restrictor 236 may be determined empirically by testing the fluid flow of selected fluids at conditions of interest.

Referring to FIG. 4B, in one embodiment, flow restrictor 236 extends through a side 210a of fluid delivery device 110. In one embodiment, flow restrictor 236 extends through hydraulic bolus chamber 216 such that hydraulic bolus chamber 216 is in fluid communication with hydraulic basal chamber 214 through flow restrictor 236 and hydraulic basal and bolus chambers 214, 216 are both in fluid communication with hydraulic pump chamber 318 through a nonrestrictive fluid passageway 238. In an alternative embodiment, fluid passageway 238 is restrictive in order to retard the delivery rate of the bolus dose rather than having the delivery rate be nearly equal to the rate of movement of bolus actuator 322.

With continued reference to FIG. 4B, in one embodiment, flow restrictor 236 includes a guide plug 240. In one embodiment, guide plug 240 is sealed with manifold 226 and positions flow restrictor 236 within fluid passageway 238. In one embodiment, guide plug 240 includes an opening 240a for fluidly coupling flow restrictor 236 and hydraulic bolus chamber 216. Flow restrictor 236 may be secured to manifold 226 by an adhesive. In one embodiment, guide plug 240 and flow restrictor 236 are comprised of generally translucent materials such that flow restrictor 236 may be fixed to manifold 226 by a UV curable adhesive after inserting flow restrictor 236 and guide plug 240 within manifold 226.

Referring to FIGS. 3 and 4A, when fluid delivery device 110 is activated, basal actuator 320 acts on the hydraulic fluid, increasing the pressure within hydraulic basal chamber 214. As a result of this pressure increase, the hydraulic liquid within hydraulic basal chamber 214 begins to flow through flow restrictor 236 into hydraulic bolus chamber 216. In one embodiment, bolus actuator 322 prevents expansion of hydraulic bolus chamber 216 and the hydraulic fluid from hydraulic basal chamber 214 flows through fluid passageway 238 and into hydraulic pump chamber 318 where the hydraulic fluid displaces third moveable barrier 234 causing the fluid within fluid reservoir 224 to exit fluid delivery device 110 at a sustained basal rate. In one embodiment, the basal rate is predetermined or preset by the manufacturer. Embodiments of fluid delivery device 110 may be used to continuously deliver a fluid over a range of time such as but limited to 1 min, 1 hr, 6 hrs, 12 hrs, 1 day, 3 days, 5 days, 10 days, one month, etc. In certain embodiments, the fluid is expelled from the fluid delivery device 110 at a basal rate selected from but not limited to: about 0.1 μl to about 10 μl per hour, about 10 to about 100 μl per hour, about 100 μl per hour to about 1 ml per hour, about 1 ml to about 100 ml per hour, or about 100 ml to about 200 ml per hour. In one embodiment, the basal rate of insulin u100 (i.e., 100 units of insulin per ml) is approximately 100 units/day which is 42 ul/hour or 1000 ul/24 hours. The rate and delivery period selected will depend upon the application at hand, and those of skill in the art will be able to determine the proper dosage rate for a given application.

Referring to FIG. 3, embodiments of fluid delivery device 110 may be connected to an infusion set or needle 212 through a connection point at distal end 324a of fluid reservoir 224. In alternative embodiments, needle 212 may be located on the side wall of fluid reservoir 224. Needle 212 may be substituted with any delivery device such as a lumen, a needle set, a catheter-cannula set or a microneedle or microneedle array attached by means of one or more lumens.

In one embodiment, basal flow rate is preset at the time of manufacture based on the selection of flow restrictor 236 in combination with the viscosity of the hydraulic fluid and the force supplied on hydraulic basal chamber 214. Alternatively, the length and/or diameter of flow restrictor 236 can be adjusted on demand to alter the basal flow rate. In other embodiments, flow restrictor 236 may be adjustable in size, as by means of an adjustable iris-type aperture or telescoping restrictor passage miniature valve or paired gating slits (not shown). In an alternate embodiment, an electrical motor or piezoelectric device (not shown) may be used to open or close the aperture, thus affecting the rate at which hydraulic fluid flows into hydraulic pump chamber 318 and displaces third moveable barrier 234.

The hydraulic fluid may be any non-compressible, flowable material such as gel or a collection of miniature solid beads. In one embodiment, the hydraulic fluid is an ultrapure, bio-inert material. In one embodiment the hydraulic fluid is silicon oil. Useful viscosity of the hydraulic fluid is limited at its upper bound by the size of flow restrictor 236. At its lower bound, the hydraulic fluid must be viscous enough that the flow of the hydraulic fluid can remain highly regulated by the combination of the pressure from basal actuator 320 and the size of flow restrictor 236 under a wide range of environmental conditions, especially in the presence of low atmospheric pressure and/or high ambient temperature (where viscosity tends to decrease).

As used herein, "high viscosity" means the working hydraulic fluid has a viscosity grade of at least about ISO VG 20, or at least about ISO VG 32, or at least about ISO VG 50, or at least about ISO VG 150, or at least about ISO VG 450, or at least about ISO VG 1000, or at least about ISO VG 1500 or more. In one embodiment the hydraulic fluid is very high viscosity fluid. As used herein, "very high viscosity" means the working hydraulic fluid has a viscosity of from about 80,000 to about 180,000 cPs. In one embodiment the hydraulic fluid is ultra high viscosity fluid (e.g., from about 180,000 to about 200 cPs). In one embodiment, the hydraulic fluid has a viscosity of 100,000 centiStokes.

Figure 5A:
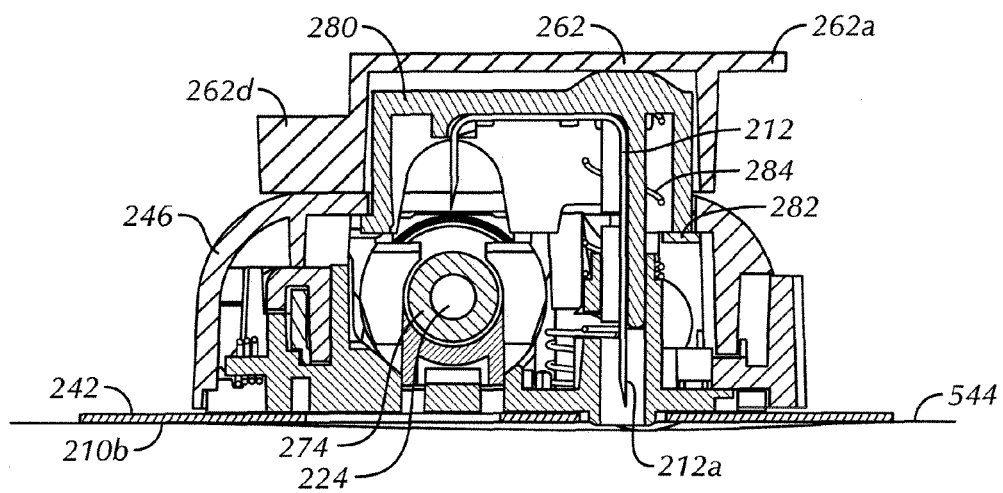
FIG. 5A is a side cross sectional view of a basal hydraulic chamber and biasing members of the fluid delivery device shown in FIG. 1 taken along line 5A-5A of FIG. 1 shown in an initial position.
Figure 5B:
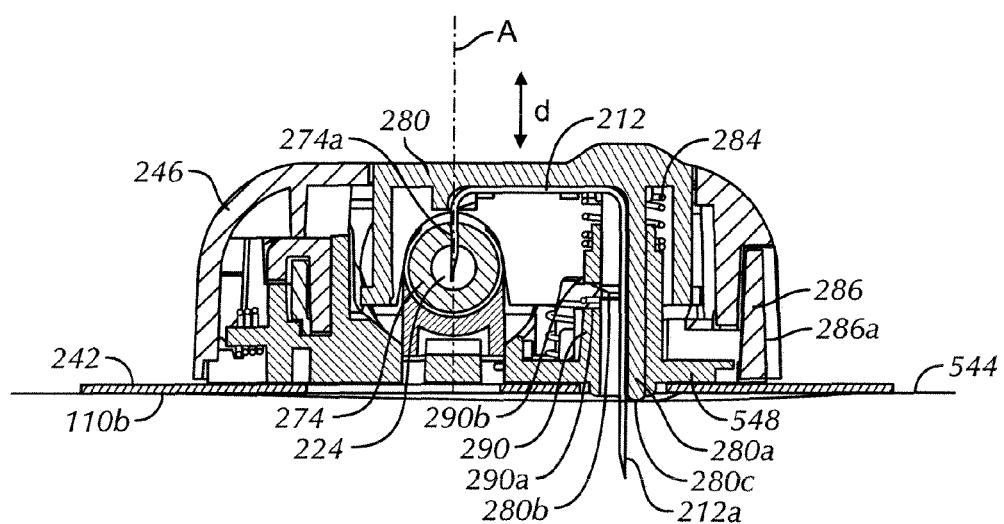
FIG. 5B is the side cross sectional view of FIG. 5A shown in the engaged position.

Referring to FIGS. 5A and 5B, in order reduce the influence of the outside environmental temperature on the temperature of the hydraulic fluid, one or more additional features may be incorporated into the device to insulate and isolate the hydraulic fluid from the outside environment. In one embodiment, manifold 226 and housing 246 may be separated by an open air gap in the areas that face toward the outside environment. To further isolate the hydraulic liquid, the air gap between the hydraulic basal chamber and housing 246 can be divided into separate air pockets to further decouple or insulate the air within this gap. In one embodiment, fluid reservoir 224 is thermally isolated from a user's skin surface 544. In one embodiment, the air gap within housing 246 substantially surrounds fluid reservoir 224 to keep the fluid at a cooler temperature than skin surface 544.

Referring to FIGS. 3 and 4A, in one embodiment, basal actuator 320 exerts a force on hydraulic basal chamber 214 to pressurize the hydraulic fluid. Basal actuator 320 may be any device that applies a force on hydraulic basal chamber 214 such as, but not limited to a peristaltic actuator, miniaturized bellows crank, or paired rollers bearing on hydraulic basal chamber 214, ratchet or stepper motor driven units that compress plates or other structures bearing on the hydraulic basal chamber 214, electrically driven or piezoelectric mechanisms, expanding gas volume, thermal energy, or any other device or process capable apply a pressure, either directly or indirectly, to the fluid being delivered. In one embodiment, basal actuator 320 is open loop such that no electronics are required and fluid delivery device 110 may be purely mechanical.

In one embodiment, basal actuator 320 is comprised of one or more biasing members such as a first biasing member 250 and a second biasing member 252. In one embodiment, first and second biasing members 250, 252 are springs. In one embodiment, first and second biasing members 250, 252 are helical compression springs. The force exerted by a spring in a compressed state at the start of travel is greater than the force exerted by the spring in a less compressed state toward the end of travel. The resulting force differential can impact the flow of hydraulic fluid within fluid delivery device 110 and thus impact the flow of the fluid being delivered.

In one embodiment, the difference in the force exerted by first and second biasing members 250, 252 between the initial compressed state and the less compressed state is reduced, thus reducing the amount of possible variation in the device's ability to achieve a sustained fluid delivery rate. In one embodiment, the force differential between the compressed and less compressed state is minimized by reducing the spring rate (force/deflection) of the spring. In one embodiment, this is achieved by utilizing multiple, coaxial stacked biasing members. In one embodiment, the cross sectional area of hydraulic basal chamber 214 is larger than the cross sectional area of hydraulic pump chamber 318 to move third moveable barrier 234 a greater axial distance than the axial distance traveled by first moveable barrier 230 (see e.g. FIG. 4A). Reducing the spring force attenuation that occurs over the total travel of the spring (stroke) during operation and maintaining a more constant spring force on the hydraulic fluid produces a more consistent flow of fluid from fluid delivery device 110.

Referring to FIGS. 2 and 4A, in one embodiment, second biasing member 252 is coupled to first biasing member 250 in series and at least partially overlaps first biasing member 250. In one embodiment, first biasing member 250 is co-axial with second biasing member 252. In one embodiment, a proximal end 250a of first biasing member 250 is coupled to housing 246. In one embodiment, proximal end 250a abuts against a stop 254 extending from base 248. In one embodiment, a sleeve 256 couples a distal end 250b of first biasing member 250 with a proximal end 252a of second biasing member 252, sleeve 256 having a length generally equal to the length of overlap between first and second biasing members 250, 252.

Basal actuator 320 may include a plunger 258 extending through first and second biasing members 250, 252. In one embodiment, distal end 258a of plunger 258 has a radially outwardly extending flange 258b. Flange 258b of plunger 258 may engage first moveable barrier 230 and distal end 252b of second biasing member 252. A proximal end 258c of plunger 258 may be releaseably coupled with stop 254. Plunger 258 may extend through stop 254 and be releaseably coupled to housing 246 with a pin 260. In one embodiment, pin 260 extends through housing 246 and at least partially through plunger 258 and abuts against stop 254 such that pin 260 prevents plunger 258 from extending further into hydraulic basal chamber 214 due to the force of first and second biasing members 250, 252 and can be removed from outside of housing 246. In one embodiment, pin 260 is tapered to facilitate easier removal of pin 260. Pin 260 may be coupled with a button cover 262 such that removal of button cover 262 releases plunger 258 in one step by the user as described further below.

In one embodiment, fluid delivery device 110 is capable of dispensing fluid continuously or near continuously at a basal rate, as well as dispensing a supplementary amount of fluid or bolus on demand or under patient control. Fluid delivery device 110 may allow for the user to deliver multiple discrete bolus amounts without the user having to look at fluid delivery device 110 or set the bolus amount for delivery under and through the user's shirt (not shown). Each bolus dose may require two distinct motions to deliver the bolus dose. In one embodiment, a multiple button sequence to be performed by the user to improve deliberate and correct bolus dosing. In a preferred embodiment, the bolus delivery is operated by a cyclic (i.e., common, consistent, routine) mechanical system in which the user executes the same action one or multiple times to achieve one or multiple bolus doses per cycle.

Referring to FIG. 4A, in one embodiment, fluid reservoir 224 is initially filled with a quantity of the fluid to be delivered to the user. In another embodiment, fluid reservoir 224 may be filled by the user prior to use. In one embodiment, fluid cartridge 228 of fluid reservoir 224 is comprised of a rigid material. In one embodiment, fluid cartridge 228 is comprised of glass.

In the case of a medicament, the quantity of fluid may be pre-determined by a medical professional in order to provide the necessary dosing over a pre-determined period of time. The volume of fluid reservoir 224 may be about 100 µl, 500 µl, 1 ml, 3 ml, 5 ml, 10 ml, 30 ml, 50 ml, 100 ml or more. Referring to FIG. 2, fluid cartridge 228 may include a septum 274 within the distal end of fluid cartridge 228. In one embodiment, septum 274 acts as a stopper. In other embodiments, septum 274 may be at least portion of the sidewall (not shown). In one embodiment, fluid cartridge 228 includes a spacer 276 on the hydraulic fluid side of third moveable barrier 234 such that the size of fluid cartridge 228 may adapt to a range of fluid volumes by varying the size of spacer 276. In one embodiment, spacer 276 may be brightly colored to help indicate the level of fluid within fluid cartridge 228. Fluid cartridge 228 may include a seal 278 that has an opening 278a (see FIG. 2) such that seal 278 seals fluid cartridge 228 to manifold 226 while allowing the hydraulic fluid to pass through to either spacer 276 and/or third moveable barrier 234.

In one embodiment, septum 274 is composed of a flexible material such as rubber and fits within fluid cartridge 228, forming a seal on the end opposite third moveable barrier 234. Septum 274 may be a hollow cylinder open only at the end that is installed in fluid cartridge 228. Septum 274 may remain stationary and is positioned to align with needle 212. When needle 212 pierces the side of septum 274, the fluid path between fluid delivery device 110 and the outside environment is opened, allowing the fluid to flow from fluid delivery device 110. In one embodiment, septum 274 is exposed through a side of housing 246 to allow for the user to fill fluid reservoir 224. Septum 274 may have a hardness sufficient to allow needle 212 to move relative to the remainder of fluid delivery device 110 as described in further detail below. In one embodiment, septum 274 has a hardness of 50 shore A. In one embodiment, septum 274 has a hardness of 40 shore A.

Referring to FIGS. 5A and 5B, in one embodiment, fluid delivery device 110 has multiple operable states. In a first operable state or storage position (FIG. 5A), needle 212 is not engaged or is separated from fluid reservoir 224 and does not extend from housing 246 (i.e. not inserted into the body). In a second operable state or engageable position (not shown), needle 212 is able to be engaged with fluid reservoir 224. In a third operable state or engaged or activated position (FIG. 5B), needle 212 is in fluid communication with the fluid to be delivered and is inserted into the body or available for insertion into the body. In a fourth operable state or disengaged or disposable position (not shown), needle 212 is again separated from the fluid to be delivered, is not inserted into the body, and is fixedly (lockably) retained within housing 246.

In one embodiment, button cover 262 shrouds needle 212 preventing accidental depression of needle 212 during handling and shipping of fluid delivery device 110. In one embodiment, button cover 262 includes a flange 262a to facilitate grasping and removing button cover 262 by the user. In one embodiment, button cover 262 has a projection 262b for coupling with pin 260. Button cover 262 may include indicia 262c such as the word "Remove" to indicate what the user should do with button cover 262 (See FIG. 2). In one embodiment, button cover 262 includes a tab 262d for providing leverage against housing 246 as button cover 262 is removed by holding flange 262a on the opposite side of button cover 262. In one embodiment, when button cover 262 is removed, a needle button 280 coupled to needle 212 is exposed (FIG. 5B).

In one embodiment, needle 212 is fixed to needle button 280. In one embodiment, needle 212 is heat staked to needle button 280 at one or more points. In other embodiments, needle 212 is moveable relative to needle button 280. In one embodiment, removal of button cover 262 simultaneously removes pin 260 from basal actuator 320 to release or activate basal actuator 320 such that it acts on the hydraulic fluid. Thus, in preferred embodiments, button cover 262 performs the dual functions of shrouding and protecting needle button 280 to prevent unintentional activation of needle 212 and simultaneously controls activation of basal actuator 320.

In one embodiment, needle button 280 deploys needle 212 when depressed (FIG. 5A). Needle button 280 may be spring biased away from septum 274. In one embodiment, needle button 280 is spring biased by a compression spring 284 as described further below. In one embodiment, needle 212 extends from fluid reservoir 224 through the pierceable member or septum 274 at a connection point 274a and out of housing 246. Needle 212 may be moveable relative to septum 274 or fluid delivery device 212 may move relative to needle 212 such that when needle 212 extends into skin surface 544 in the engaged position, movement of needle 212 relative to the user caused by movement of fluid delivery device 110 is reduced. Minimizing the movement of needle 212 relative to the user may help to reduce pain or "pinching" caused by needle 212.

In one embodiment, needle 212 is configured to translate in a direction perpendicular to septum 274, and pivot about connection point 274a in all directions. In one embodiment, the pivot of needle 212 about connection point 274a is within the boundaries of an imaginary hour glass shaped path (not shown) proximate septum 274. In one embodiment, the entire needle 212 is configured to pivot about connection point 274a due to the flexibility of septum 274 and is limited by the connection between needle button 280 and housing 246. In one embodiment, needle 212 is configured to be entirely within or at least shrouded by housing 246 and disengaged from fluid reservoir 224 in an initial position and fluidly coupled with fluid reservoir 224 and extending from housing 246 in an engaged position. In one embodiment, needle 212 is configured to pierce pierceable member 274 after extending from housing 246 when moving needle 212 from the initial position to the engaged position such that the fluid does not exit onto skin surface 544 and interfere with the adhesion of adhesive patch 242. In one embodiment, needle 212 is configured such that needle 212 pierces skin surface 544 approximately simultaneously to when needle 212 pierces pierceable member 274.

In one embodiment, needle 212 is generally j-shaped such that its two ends are pointing in the same direction but are axially and laterally spaced from one another. In one embodiment, septum 274, or at least a surface tangent to the connection point 274a, is generally parallel to a bottom surface 110b of the housing from which needle 212 extends in the engaged position. In one embodiment, needle 212 is a microneedle. In one embodiment, needle 212 is a fine gauge needle. In one embodiment, needle 212 is a 30 gauge needle. In one embodiment, both ends of needle 212 are beveled to help facilitate piercing of septum 274 and skin surface 544. In one embodiment, needle 212 is configured to rotate about an imaginary axis A that extends through connection point 274a perpendicular to septum 274 as shown in FIG. 5B such that fluid delivery device 110 may rotate about the axis A without, or at least reduces, the end of needle 212 extending into the user moving in an arched path.

In one embodiment, once needle 212 is in the engaged position needle button 280 is locked into place and the fluid in fluid reservoir 224 is in liquid communication with the outside environment (e.g., the body) via needle 212. Locking member 288 may be configured to keep the first and second ends of needle 212 disengaged from the user and fluid reservoir 224 and contained within housing 246 in a locked position upon moving needle 212 from the engaged position (FIG. 5B) to the locked position. In the locked position, needle 212 may be kept from redeployment or engagement such that housing 246 acts as its own sharps container. In one embodiment, needle 212 is moved to the locked position through use of a needle release or needle release button 286.

Figure 6:
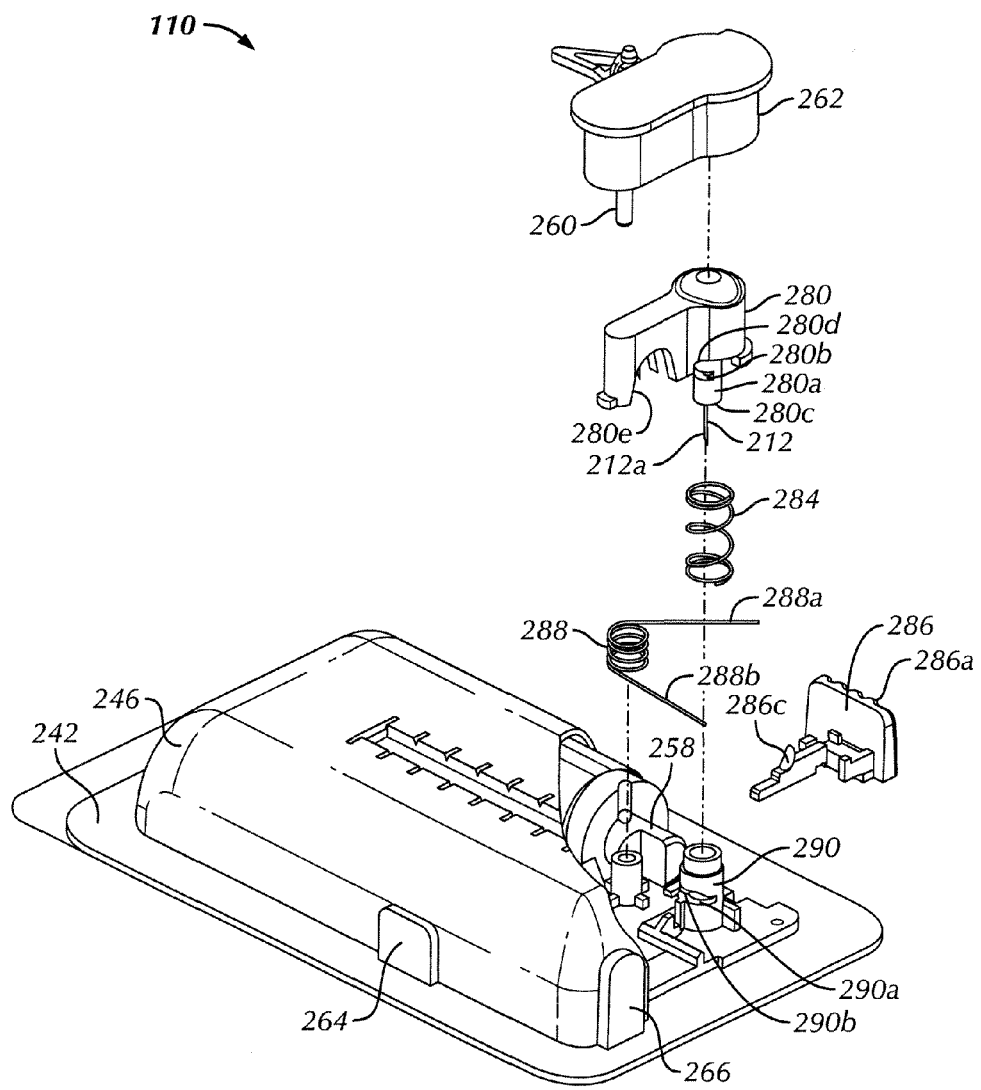
FIG. 6 is a partially exploded cut away view of a lock out assembly of the fluid delivery device of FIG. 1.

Referring to FIG. 6, in certain embodiments, spring 284 is located between needle button 280 and base 248 and surrounds a boss or sleeve 280a of needle button 280 extending partially over needle 212. In one embodiment, spring 284 becomes compressed when needle button 280 is locked in the depressed, engaged or inserted position (FIG. 5B) to bias needle button 280 away from septum 274. Needle button 280 may be retained in the inserted position by a locking member 288 as described further below. Locking member 288 may be released when the user is finished with fluid delivery device 110. In one embodiment, prior to removing fluid delivery device 110 from the body, the user activates needle release button 286 to retract needle 212 from the user and into housing 246. The bottom of housing 246 is also referred to as base 248 but both may be collectively referred to as housing 246 herein. Anything interior to the entire outer surface of fluid delivery device 110 may be referred to as into or within housing 246 as used herein. In other embodiments, needle 212 is automatically retracted after fluid reservoir 224 is substantially empty or automatically upon removal of fluid delivery device 110 from skin surface 544 as described further below.

In one embodiment, locking member 288 is a spring. In one embodiment, locking member 288 is comprised of a helical torsion spring. In one embodiment, locking member 288 biases needle release button 286 and interacts with features of needle button 280 and base 248 to releaseably retain needle 212 in the depressed or inserted position (FIG. 5B) and unreleaseably locked in the lock-out position.

In one embodiment, locking member 288 is coupled to or engageable with needle release button 286. In one embodiment, needle release button 286 has a surface 286a exposed through housing 246. In one embodiment, surface 286a of needle release button 286 is exposed through an aperture in housing 246 on a first side of housing 246. In one embodiment, needle release button 286 is not laterally aligned with bolus release button 264 such that the user can grip bolus release button 264 and an opposing housing surface between a thumb and a finger to activate bolus release button 264 without inadvertently engaging needle release button 286. In one embodiment, needle release button 286 may include at last one projection 286b extending from the surface to help facilitate grip with the user's hand. In one embodiment, at least one projection 286b is ramped (see FIG. 6) to further facilitate grip and help indicate to the user by feel which direction needle release button 286 should be urged.

Referring to FIG. 6, in one embodiment, sleeve 280a surrounds needle 212 and locking member 288 is spring biased toward sleeve 280a. In one embodiment, sleeve 280a has at least one abutment surface configured to engage with locking member 288 to prevent at least one of engaging and disengaging needle 212. In one embodiment, at least one abutment surface includes a first abutment surface 280b and a second abutment surface 280c.

In one embodiment, first abutment surface 280b is axially spaced along needle 212 from the second abutment surface 280c. In one embodiment, first abutment surface 280b is a radially inwardly extending groove. In one embodiment, second abutment surface 280c is distal end of sleeve 280. In other embodiments, first and second abutment surfaces 280b, 280c are any surface such as a projection or groove that axially engages with locking member 288. In one embodiment, base 248 includes an upwardly extending boss or guide 290 for receiving and guiding sleeve 280a and engaging with locking member 288. In one embodiment, guide 290 loosely fits over sleeve 280a to allow some nonaxial movement or pivot of needle button 280 relative to guide 290 for the pivoting of needle 212 as described above. Guide 290 may include a groove 290a configured to receive locking member 288. In one embodiment, groove 290a aligns with first abutment surface 280b in the engaged position (FIG. 5B) and aligns with second abutment surface 280c in the locked-out position. In one embodiment, locking member 288 engages with first abutment surface 280b to releaseably retain needle 212 in the engaged position (FIG. 5B) and locking member 288 engages with second abutment surface 280c to unreleaseably retain needle 212 in the locked position. In one embodiment, needle release button 286 is configured to position locking member 288 into the locked position upon disengaging needle 212 from the user.

Referring to FIG. 6, in one embodiment, locking member 288 is configured to provide an audible feedback upon retaining needle 212 in the engaged position so the user is assured that needle 212 has been fully deployed and in the engaged position. In one embodiment, guide 290 includes a projection 290b that facilitates creating an audible "click" by sliding locking member 288 over and into groove 290a and first abutment surface 280a. In one embodiment, projection 290b is selectably engageable with locking member 288. In one embodiment, projection 290b is a ramped surface 286c. In one embodiment, locking member 288 is biased against guide 290 above groove 290a and depressing needle button 280 engages a surface 280d with locking member 288 and slides locking member 288 down guide 290 over projection 290b and into the aligned groove 290a and first abutment surface 280b. In one embodiment, needle button 280 includes a cutout 280e to fit over septum 274. In one embodiment, cutout 280e is loosely sized to the contour of septum 274 to support needle 212 relative to housing 246 but allows for the movement of needle 212 described above.

Figure 7A:
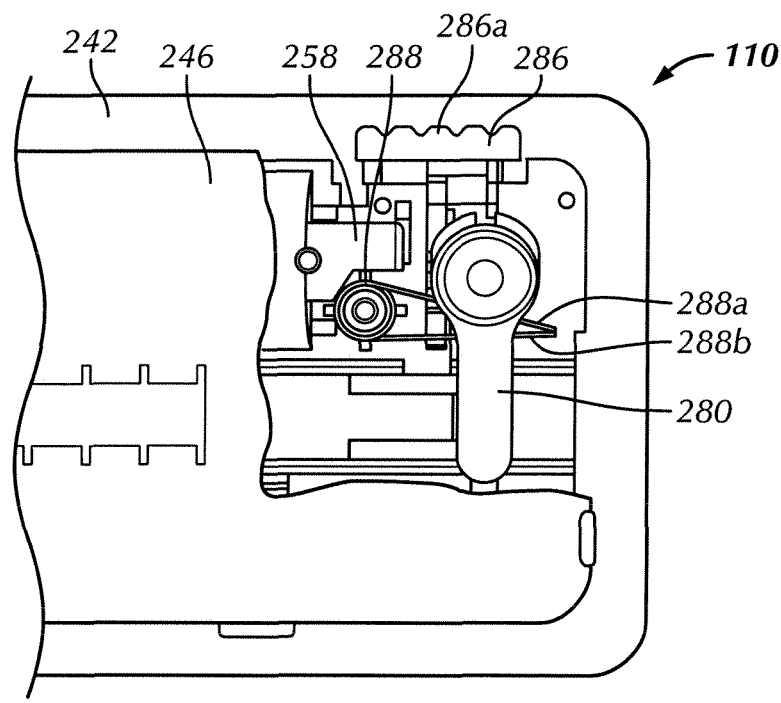
FIG. 7A is a top, partially cut away view of a lock out assembly of the fluid delivery device of FIG. 1 in an initial or ready to be engaged position.
Figure 7B:
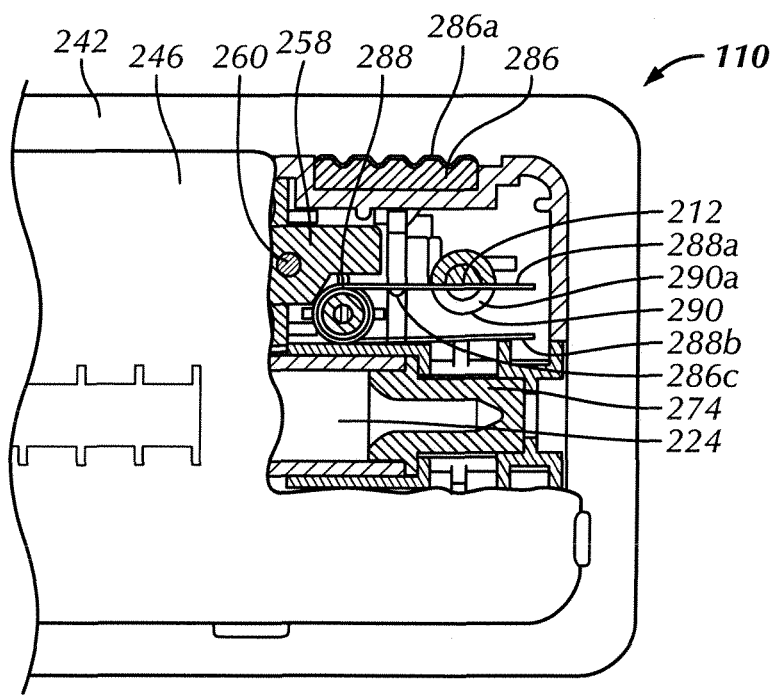
FIG. 7B is a top, partially cut away view of a lock out assembly of the fluid delivery device shown in FIG. 1 in a locked out position.
Figure 11A:
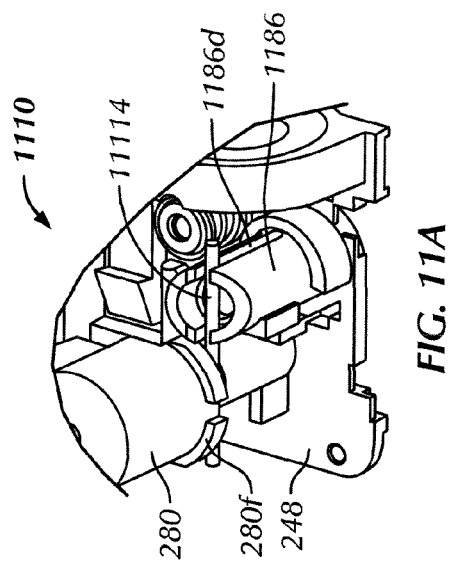
FIGS. 11A-11D are various partial views of a fluid delivery device in accordance with an exemplary embodiment of the present invention in an initial position.
Figure 11D:
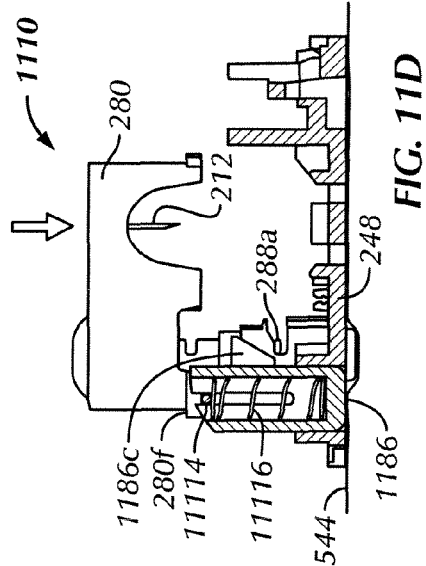
Figure 11B:
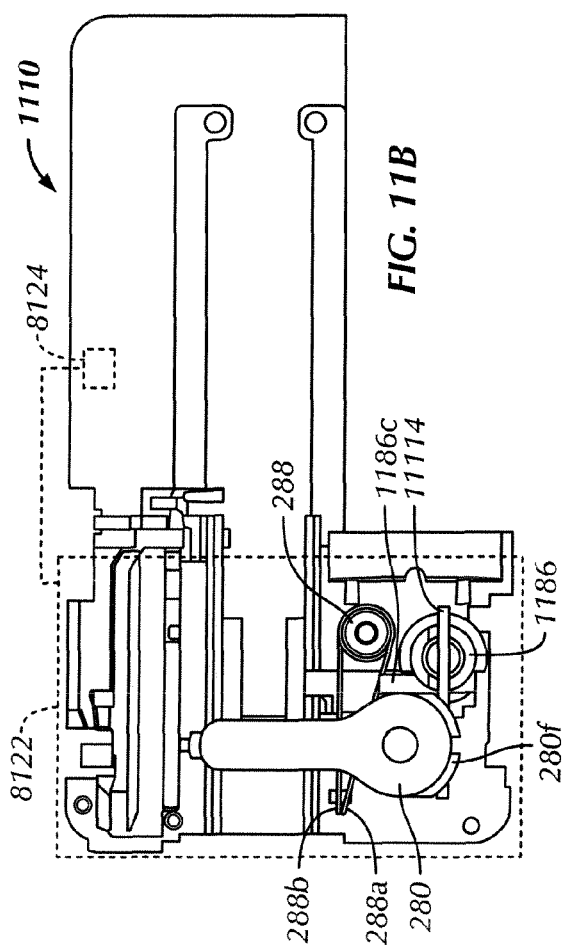
Figure 11C:
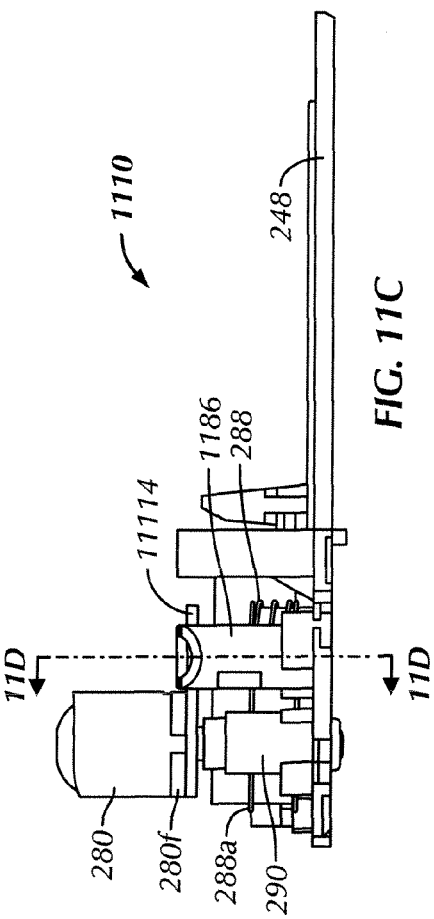
Figure 12A:
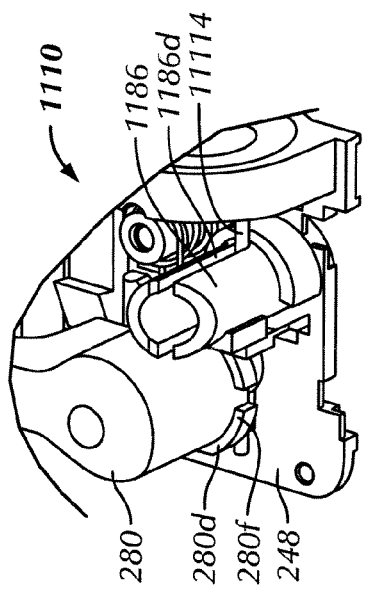
FIGS. 12A-12D are various partial views of the fluid delivery device shown in FIGS. 11A-11D in a delivery position.
Figure 12D:
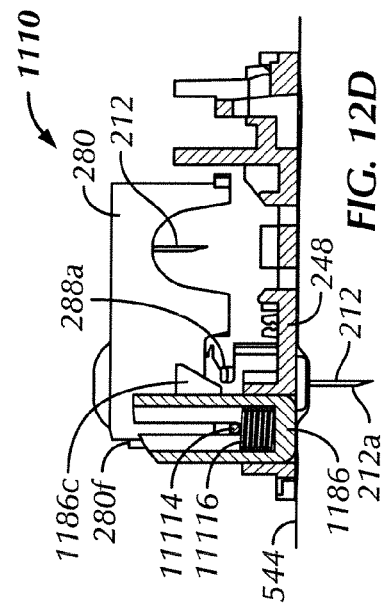
Figure 12B:
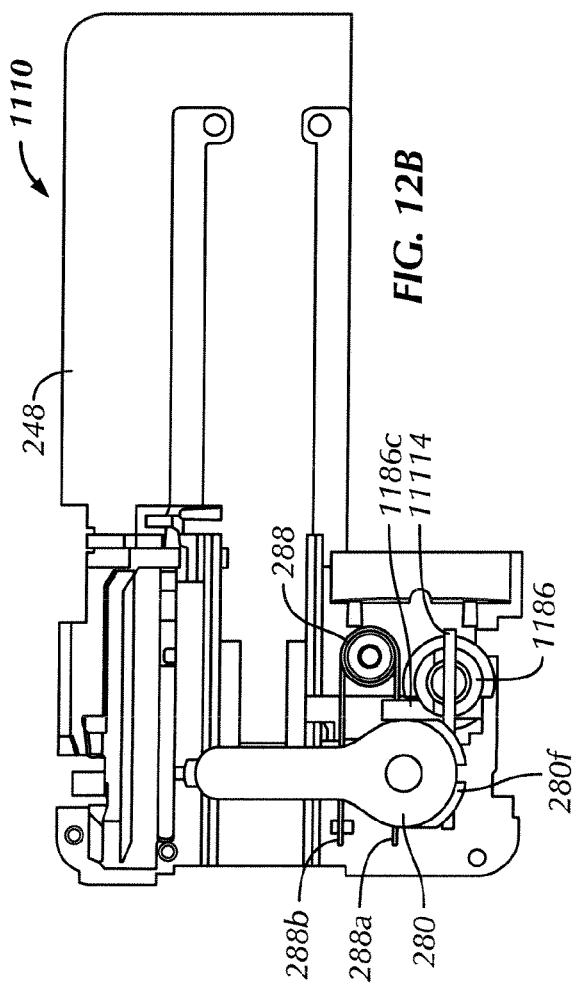
Figure 12C:
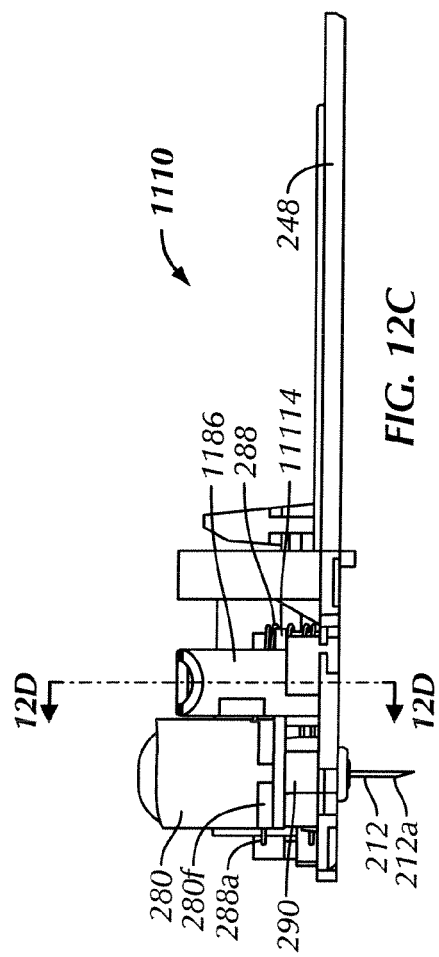

In one embodiment, when the user depresses needle button 280, a free end or first arm 288a of locking member 288 is moved from its initial preloaded position against guide 290 and into aligned groove 290a and first abutment surface 280b. When needle release button 286 is depressed ramped surface 286c may force first arm 288a of locking member 288 from first abutment surface 280a momentarily, allowing needle button 280 to retract to the upright or initial position as a result of the force from spring 284. As the user continues to press needle release button 286, the end of first arm 288a may abut a surface within housing 246, preventing further rotation. The mid section of first arm 288a may then deflect over ramped surface 286c of needle release button 286 allowing first arm 288a to spring back into groove 290a (FIG. 7B). Second abutment surface 280c of needle button 280 may then be axially above first arm 288a extending across guide 290 preventing needle button 280 and needle 212 from further translation or re-depression/re-deployment (FIG. 7B). In one embodiment, needle release button 286 is configured to release locking member 288 only after completing two distinct motions to prevent accidental release of locking member 288.

In some embodiments, fluid delivery device 110 includes an adhesive to facilitate attachment of fluid delivery device 110 to skin surface 544 of the user. The adhesive strength should preferably be sufficient to adhere fluid delivery device 110 to skin surface 544 of the user for the duration of treatment with the drug-filled fluid delivery device 110. Thus, adhesive strength may vary depending on the duration of treatment (e.g., 72 hours, 48 hours, 24 hours, 18 hours, 12 hours, etc.). Moreover, the adhesive should be such that fluid delivery device 110 is easily removable without undue discomfort or pain or difficulty upon completion of use. In some embodiments, the adhesive may be relieved in certain areas, e.g., in the area of the hydraulic basal chamber 214 (see e.g. area 242a in FIG. 2), fluid reservoir 224 (see e.g. area 242b in FIG. 2) and/or proximate needle 212 (see e.g. area 242c in FIG. 2), to facilitate contact of fluid delivery device 110 with skin surface 544 of the user.

The adhesive may be combined with a pad to form an adhesive patch 242. In one embodiment, adhesive patch 242 is a non-woven foam pad. In one embodiment, adhesive patch 242 is comprised of a medical foam adhesive manufactured by 3M®. In one embodiment, adhesive patch 242 is comprised of 3M® 9776 material. In one embodiment, the outer dimension of adhesive patch 242 extends beyond the outer dimensions of housing 246 to allow greater adhesive surface area and/or greater flexibility of adhesive patch 246 to contour to the user's body shape. In certain embodiments, extended area is, for example, about 0.010 inches, 0.100 inches, 0.250 inches, 0.500 inches or more from housing 246. Adhesive patch 242 may be capable of movement (e.g. flexing, stretching) in multiple orientations to improve comfort of wear and reduce pinching or tightness or the wearer's perception of pinching or tightness. In one embodiment, the adhesive is initially covered by a removable film 292 (see FIG. 2). In one embodiment, film 292 includes a tab 292a extending outwardly from adhesive patch 242 to facilitate removal from adhesive patch 242 just prior to applying fluid delivery device 110 to skin surface 544.

In exemplary use, the user removes fluid delivery device 110 from a storage package (not shown). The user may then fill fluid cartridge 228 with the fluid. In one embodiment, fluid cartridge 228 is pre-filled. Once fluid cartridge 228 is filled, the user may remove button cover 262 exposing needle button 280 and simultaneously activating basal actuator 320. The user may then remove film 292 from adhesive patch 242 and place fluid delivery device 110 on skin surface 544. In other embodiments, fluid delivery device 110 is placed on skin surface 544 before removing button cover 262. Once fluid delivery device 110 is on skin surface 544 and button cover 262 is removed, the user may then depress needle button 280 to engage needle 212 (see FIG. 5B) and fluidly couple the user and fluid reservoir 224. Once needle 212 is engaged and when appropriate, the user may then activate bolus release button 264 and then activate bolus button 266 to deliver a bolus dosage. Once the delivery period (e.g. 24 hours) is complete or the user otherwise wants to remove fluid delivery device 110, the user depresses needle release button 286 to retract needle 212 into housing 246. Once needle 212 is shrouded by housing 246, the user may then remove fluid delivery device 110 from skin surface 544, dispose fluid delivery device 110 and repeat the above steps to install a fresh fluid delivery device 110.

Referring to FIGS. 8A-13D, in some embodiments, fluid delivery device 810 may include an automatic needle retraction mechanism 8122 (see FIG. 8A) configured to automatically (i.e. without any additional action by the patient) retract delivery end 212a of needle 212 into the housing 246 upon completion of delivery and/or premature removal of fluid delivery device 110 from skin surface 544. In other embodiments, needle retraction mechanism 8122 is provided in addition to needle release button 286 such that the user may alternatively chose to selectively retract needle 212 into housing 246 using needle release button 286 as described above prior to triggering an automatic retraction of needle 212.

In one embodiment, needle retraction mechanism 8122 is configured to automatically withdraw delivery end 212*a* of needle 212 into housing 246 upon actuator 320 moving from a first position to a second position. In one embodiment, fluid is delivered to the user in the first position (see e.g., FIGS. 9A-9D) and has completed delivery in the second position (see e.g., FIGS. 10A-10D). In one embodiment, fluid reservoir 224 is substantially empty in the second position. In one embodiment, basal actuator 320 reaches an end of travel in the second position.

Referring to FIGS. 8A-10D, fluid delivery device 810 is similar to embodiments of fluid delivery device 110 described above with the exception that needle release button 286 may be replaced by needle retraction mechanism 8122 that has a needle release 886 to retract needle 212 (not shown in FIGS. 8A-13D for clarity of the other features) into housing 246 upon completion of delivery.

Upon completion of fluid delivery, needle release 886 may automatically release locking member 288 causing needle 212 to retract into housing 246 by coupling basal actuator 320 to needle release 886. In one embodiment, needle release 886 is spring biased relative to housing 246 by a biasing member 8112. In one embodiment, biasing member 8112 is a torsion spring. In one embodiment, biasing member 8112 includes a first end 8112*a* coupled to needle release 886 biasing needle release 886 inwardly toward locking member 288 in an initial position (FIGS. 8A-8D) and a second end 8112*b* attached to housing 246. A lock release 8114 may be attached to basal actuator 320 and moveably coupled with needle release 886 in the initial and delivery positions (FIGS. 8A-9D) and detached from needle release 886 in the locked out or completed position (FIGS. 10A-10D) such that lock release 8114 moves along with basal actuator 320 and disengages from needle release 886 at a predetermined position of basal actuator 320.

In one embodiment, lock release 8114 extends from proximal end 258*a* of plunger 258. In one embodiment, lock release 8114 extends through needle release 886 such that lock release 8114 prevents biasing member 8112 from moving in the initial (FIGS. 8A-8D) and delivery (FIGS. 9A-9D) positions. In one embodiment, lock release 8114 extends through an upwardly extending groove in needle release 886. In other embodiments, lock release 8114 may extend through a hole in needle release 886. In one embodiment, lock release 8114 is a cylindrically shaped rod. In other embodiments, lock release 8114 is any suitable shape such as rectangular or triangular.

Lock release 8114 may have a predetermined length such that when plunger 258 reaches the end of its travel thereby concluding delivery of the fluid to the patient through needle 212 in the completed position (FIGS. 10A-10D), lock release 8114 automatically disengages from needle release 886 allowing biasing member 8112 to move needle release 886 inwardly toward locking member 288. Needle release 886 may then disengage locking member 288 from the needle assembly such that the biased needle 212 is automatically withdrawn from the body and is retained in housing 246 as described in the above embodiments. In one embodiment, needle release 886 includes a ramped projection 886*c* that moves locking member 288 inwardly away from boss 290 as needle release 886 is moved inwardly in the completed position (FIGS. 10A-10D) similar to needle release button 286 as described above.

In some embodiments, the needle assembly (e.g., button 280 and needle 212) is spring biased toward the refracted position but is retained in the delivery configuration, by for example, locking member 288 as described above, and is automatically, as opposed to manually or selectably, released by a release mechanism. In some embodiments, locking member 288 returns to lock delivery end 212*a* of needle 212 within housing 246 similar to the embodiments described above. In other embodiments, a separate device or apparatus from locking member 288 retains delivery end 212*a* of needle 212 within housing 246 following retraction. In other embodiments, needle retraction mechanism 8112 functions without a biasing member and includes for example a rack and pinion configuration controlled by an electric motor.

In one embodiment, needle 212 is retained within housing 246 to act as its own sharps container preventing further use of needle 212, such as accidental needle sticks to others, after removing fluid delivery device 1110 from a patient and/or completion of delivery. Having an automatic or passive refraction of needle 212 into housing 246 may help to ensure that needle 212 is safely contained within housing 246 without having the patient have to remember to retract needle 212 using a button or other active mechanism.

In some embodiments, needle retraction mechanism 8122 is purely mechanical. In other embodiments, needle retraction mechanism 8122 is electro-mechanical. In one embodiment, needle retraction mechanism 8122 is activated to retract delivery end 212*a* of needle 212 into housing 246 upon opening or closing of one or more switches or sensors 8124. In some embodiments the switch is mechanical. In other embodiments, the switch is electrical.

In one embodiment, one or more sensors 8124 (see FIG. 8A) may be used to detect the end of delivery to trigger needle retraction mechanism 8112 to automatically retract needle 212 into housing 246. In one embodiment, one or more sensors 8124 include one or more flow sensors that are positioned in hydraulic basal chamber 214, hydraulic bolus chamber 216, and/or fluid reservoir 224 and coupled to a processor to determine when fluid delivery is complete. In one embodiment, one or more sensors 8124 include one or more position sensors that are used to detect the position of basal actuator 320, first moveable barrier 230 and/or third moveable barrier 234 (see FIG. 3). In one embodiment, needle retraction mechanism 8122 is activated to retract delivery end 212*a* of needle 212 into housing 246 after receiving a signal from one or more sensors 8124 that delivery is completed. In one embodiment, needle refraction mechanism 8122 includes any device configured to release and/or urge delivery end 212*a* of needle 212 into housing 246 after a mechanical and/or electrical switch is activated.

Referring to FIGS. 11A-13D, there are shown portions of a fluid delivery device 1110 having a needle retraction mechanism 8122. Fluid delivery device 1110 is similar to embodiments of fluid delivery device 110 described above with the exception that needle release button 286 may be replaced by needle retraction mechanism 8122. In one embodiment, needle retraction mechanism 8122 allows for refraction of needle 212 into housing 246 upon removal of fluid delivery device 1110 from skin surface 544 before delivery of the fluid is complete (i.e. a premature removal).

In one embodiment, needle retraction mechanism 8122 has a needle release 1186 to retract needle 212 into housing 246 upon removal of fluid delivery device 1110 from the user. In one embodiment, the bottom surface of housing 246 (i.e., the skin facing side of base 248) includes an adhesive, or is coupled to a pad having an adhesive, configured to releaseably couple housing 246 to a user's skin surface 544 as described above. In one embodiment, needle 212 has a delivery end 212*a* that extends from housing 246 and into skin surface 544 in a delivery configuration. In one embodiment, needle refraction mechanism 8112 is configured to automatically withdraw delivery end 212*a* of needle 212 into housing 246 upon decoupling the bottom surface of housing 246 from skin surface 544. In one embodiment, the automatic retraction of needle 212 into housing 246 upon decoupling the bottom surface of housing 246 from skin surface 544 is completely mechanical.

Referring to FIGS. 11A-13D, in one embodiment, needle release 1186 automatically (i.e. without any additional action by the patient) releases locking member 288 upon removing fluid delivery device 1110 from skin surface 544 causing needle 212 to retract into housing 246 by coupling needle button 280 to needle release 1186. In one embodiment, needle button 280 is coupled to needle release 1186 by a lock release 11114. In one embodiment, lock release 11114 is a cylindrically shaped rod. In other embodiments, lock release 11114 is any shape such as rectangular or triangular. In one embodiment, lock release 11114 abuts against a flange 280*f* extending radially outwardly from needle button 280. In other embodiments, lock release 11114 is fixedly attached or integral with needle button 280.

In one embodiment, locking member 288 is spring biased with respect to needle release 1186 by a biasing member 11116. In one embodiment, biasing member 11116 is disposed within needle release 1186. In other embodiments, biasing member 11116 is disposed over or outside of needle release 1186. In one embodiment, biasing member 11116 is a compression spring. In one embodiment, lock release 11114 is positioned within a slot 1186*d* that allows needle release 1186 to compress biasing member 11116 without moving needle release 1186 when needle release 1186 is prevented from extending through the bottom of housing 246 by the presence of skin surface 544 in the delivery position (FIGS. 12A-12D). In one embodiment, needle release 1186 includes a ramped projection 1186*c* that is positioned above locking member 288 in the initial position (FIGS. 11A-11D) and the delivery position (FIGS. 12A-12D) and is positioned below locking member 288 in the locked or disengaged position (FIGS. 13A-13D).

In one embodiment, biasing member 11116 is uncompressed in the initial position (FIGS. 11A-11D) and needle release 1186 is generally flush with the bottom of housing 246. Upon depressing needle button 280 to deploy needle 212 into the user in the delivery position (FIGS. 12A-12D) when fluid delivery device 1110 is positioned on skin surface 544, needle button 280 may urge lock release 11114 downward compressing biasing member 11116. Skin surface 544 (FIG. 12D) prevents needle release 1186 from extending downwardly through housing 246. Upon removing fluid delivery device 1110 from skin surface 544 (FIGS. 13A-13D) either at completion of fluid delivery or any time prior to complete delivery, biasing member 11114 may urge needle release 1186 downwardly through housing 246, causing ramped projection 1186*c* extending from needle release 1186 to contact and displace locking member 288 and thereby releasing the biased needle button 280 and retracting delivery end of needle 212 into housing 246. Needle 212 may then be prevented from redeployment by locking member 288 as described in the embodiments above.

In some embodiments, needle release 1186 has the reversed orientation as described above so that needle release 1186 initially extends from the bottom surface of housing 246, is urged into housing 246 during use and activates the needle release mechanism when housing 246 is decoupled from skin surface 544. In other embodiments, lock release 11114 is electrically activated using one or more sensors or switches 8124 to detect removal of housing 246 from skin surface 544 similar to needle retraction mechanisms 8112 described above. In one embodiment, one or more sensors 8124 for retraction of needle 212 into housing 246 upon removal of housing 246 from skin surface 544 include a photo sensor disposed on base 248 to detect when housing 246 is removed from skin surface 544. In one embodiment, one or more sensors 8124 for retraction of needle 212 into housing 246 upon removal of housing 246 from skin surface 544 include a capacitive sensor disposed on base 248 to detect when housing 246 is removed from skin surface 544.

Referring to FIGS. 14-27C, though fluid delivery device 110 may be assembled with an empty cartridge 228 such that cartridge 228 is filled after assembly of fluid delivery device 110, in some embodiments it may be desirable to insert a pre-filled cartridge 1428 into fluid delivery device 110 either during manufacturing or assembly of fluid delivery device 110 or by the end user. Because seal 278 may be compressible in order to form a sufficient seal between cartridge 228 and manifold 226, the material in one or more of pump chamber 318 and fluid reservoir 224 must be compressed and/or displaced if medicinal piston 234 is coupled to the hydraulic fluid either directly or through a generally incompressible member. In some embodiments, having components or volumes that are compressible within cartridge 228 and pump chamber 318 is undesirable due to rate of delivery concerns. With no or greatly reduced compressibility, insertion of a completely filled cartridge 1428 becomes difficult if not impossible without somewhere for the delivery fluid or hydraulic fluid to go.

Figure 14:
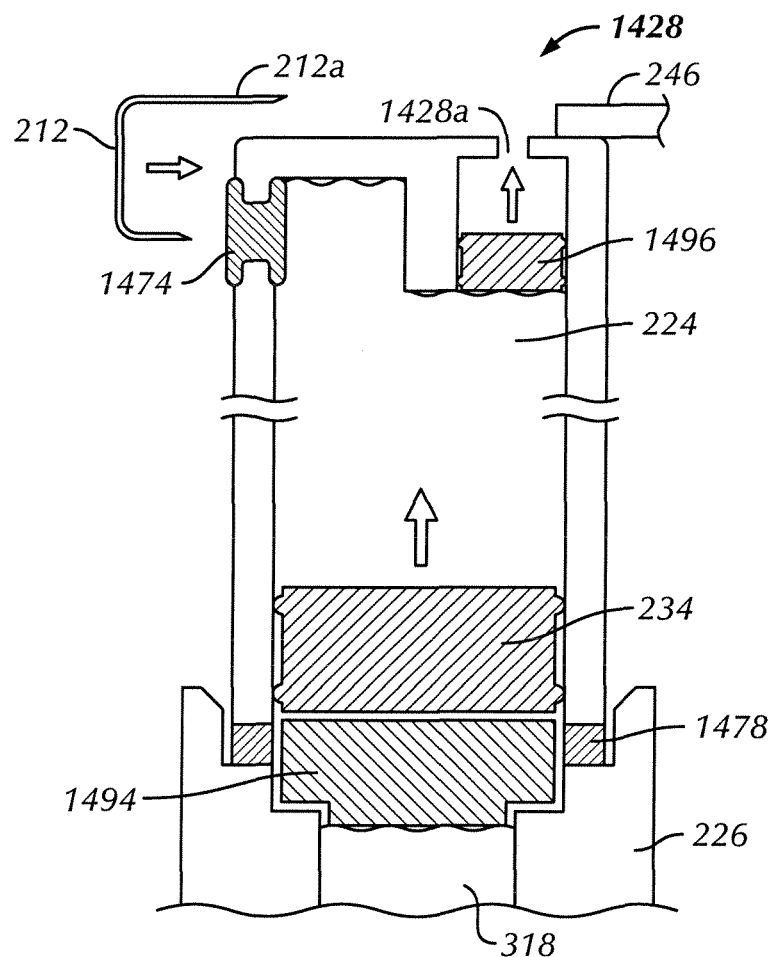
FIG. 14 is a cross sectional view of a cartridge for use with a fluid delivery device similar to the fluid delivery device shown in FIG. 1 in accordance with an exemplary embodiment of the present invention.

Referring to FIG. 14, a first exemplary pre-filled cartridge 1428 is shown. In fluid delivery device 110, the hydraulic fluid within pump chamber 318 may be covered by a cap 1494. In one embodiment, cap 1494 sits on top of the hydraulic fluid to prevent the hydraulic fluid from leaking from manifold 226 following assembly and before insertion of cartridge 1428. Cap 1494 may stay in place with respect to manifold 226 and retain the hydraulic fluid within manifold 226 without attaching cap 1494 to manifold 226. In some embodiments, a combination of surface tension between hydraulic fluid and cap 1494 and the other outlets being sealed (e.g. the basal and bolus ends) keeps cap 1494 in place.

Fluid delivery device 110 may include a seal 1478 that seals cartridge 1428 with manifold 226 once cartridge 1428 is installed. In one embodiment, seal 1478 is compressible. In one embodiment, seal 1478 is comprised of an elastomeric material. In one embodiment, seal 1478 is ring or washer-shaped. In one embodiment, cap 1494 extends axially outwardly further than the top surface of seal 1478 at least when seal 1478 is compressed by cartridge 1428 so that cap 1494 contacts medicinal piston 234 to reduce or eliminate the amount of compressible air between cap 1494 and medicinal piston 234. Cartridge 1428 may retain seal 1478 in a compressed position by having cartridge 1428 abut against a portion of housing 246 or a member otherwise fixed with respect to manifold 226.

In one embodiment, cartridge 1428 includes a septum 1474 for receiving a needle 212 during use as described in the embodiments above. In one embodiment, septum 1474 is injection molded into cartridge 1428. In one embodiment, septum 1474 is press fit into cartridge 1428. In one embodiment, cartridge 1428 includes a relief piston 1496. Relief piston 1496 may be moveable with respect to cartridge 1428. In one embodiment, to install relief piston 1496, relief piston 1496 is pressed through an aperture 1428a during manufacturing of cartridge 1428. In one embodiment, relief piston 1496 is comprised of an elastomeric material. In one embodiment, relief piston 1496 has a similar configuration as medicinal piston 234 as described above. Upon insertion of cartridge 1428, relief piston 1496 may displace a volume of air through aperture 1428a equivalent to the volume displaced by medicinal piston 234. The volume of air displaced through aperture 1428a by relief piston 1496 may be greater than the volume of fluid displaced by medicinal piston 234 upon insertion of cartridge 1428 but any excess volume displaceable through aperture 1428a after insertion of cartridge 1428 may result in travel of basal and/or bolus actuators 320, 322 without delivery of the fluid.

The pre-filled cartridges, such as cartridge 1428, may be sealed prior to use or assembly with fluid delivery device 110. In one embodiment, cartridge 1428 is provided to the user in a foil pouch (not shown). In one embodiment, cartridge 1428 and the remainder of a fluid delivery device 110 are provided in one or more sealed packages (not shown) and the user unwraps both components prior to assembly and use.

In an exemplary use, after removing cartridge 1428 and fluid delivery device 110 from their packaging, cartridge 1428 is inserted into fluid delivery device 110 until cartridge 1428 compresses seal 1478 sufficiently to seal cartridge 1428 and manifold 226 together. In one embodiment, cartridge 1428 snap-fits into place. In one embodiment, a portion of housing 246 or a member otherwise fixable with respect to manifold 226 is moved to abut cartridge 1428 and holds cartridge 1428 in the assembled position. As cartridge 1428 compresses seal 1478, medicinal piston 234 abuts cap 1494 displacing medicinal piston 234 upwardly with respect to cartridge 1428. The increase in pressure within fluid reservoir 224 caused by the force on medicinal piston 234 forces relief piston 1496 upwardly toward aperture 1428a reducing the pressure of fluid reservoir 224. Once cartridge 1428 is installed with fluid delivery device 110, needle 212 may be inserted through septum 1474 and the fluid may be delivered to the user. Once the pressure is applied (e.g. activation of either basal or bolus actuators 320, 322 (see FIG. 3)), cap 1494 may move with the hydraulic fluid in pump chamber 318 to displace medicinal piston 234 and travel with the advancement of the hydraulic fluid up into cartridge 1428.

In one embodiment, septum 1474 and needle 212 only engage after cartridge 1428 has been installed into a fluid delivery device 110. In other embodiments, needle 212 may engage with septum 1474 during or as a result of the insertion of cartridge 1428 into a fluid delivery device 110.

Figure 15:
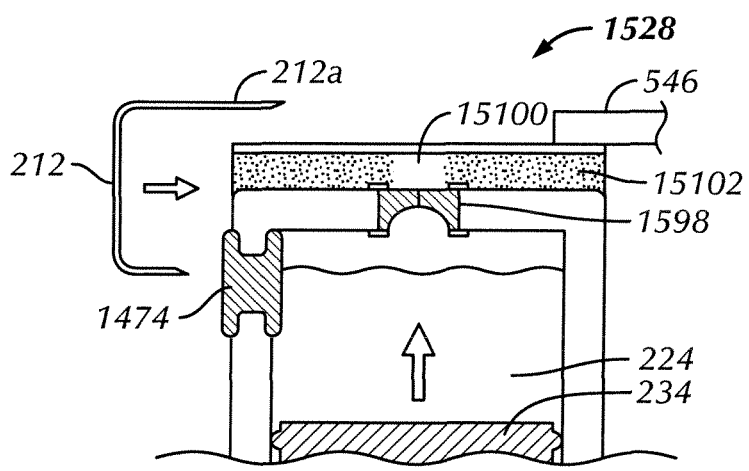
FIG. 15 is a cross sectional view of a cartridge for use with a fluid delivery device similar to the fluid delivery device shown in FIG. 1 in accordance with an exemplary embodiment of the present invention.

Referring to FIG. 15, in one embodiment, a cartridge 1528 may include a relief valve 1598 to expel air and/or fluid from fluid reservoir 224 during insertion of cartridge 1528 into a fluid delivery device 110. Because it may be undesirable to inject air into the user, the displacement of medicinal piston 234 caused by cap 1494 during insertion of cartridge 1528 may help to expel any air within fluid reservoir 224. Relief valve 1598 may allow for the air within fluid reservoir 224 to be expelled during insertion of cartridge 1528. In one embodiment, relief valve 1598 is comprised of a slit within an elastomeric member that is press fit into an aperture in cartridge 1528. Relief valve 1598 may also serve as a safety valve to prevent build up of pressure in fluid reservoir 224 caused by for example an accidental deployment of bolus actuator 322 before activation of needle 212. Relief valve 1598 may be used independently or in combination with any of the features described herein.

In one embodiment, cartridge 1528 includes a fluid trap 15100 to contain any fluid that is expelled through relief valve 1598. Fluid from fluid reservoir 224 may be expelled through relief valve 1598 if fluid reservoir 224 contains less than the anticipated amount of air and/or cartridge 1528 is inserted in a non-vertical manner such that the air rises to the top of cartridge 1528 proximate relief valve 1598. In one embodiment, fluid trap 15100 includes an absorbable member 15102 to help contain any fluid expelled from fluid reservoir 224. In one embodiment, absorbable member 15102 is comprised of cotton.

Figure 16:
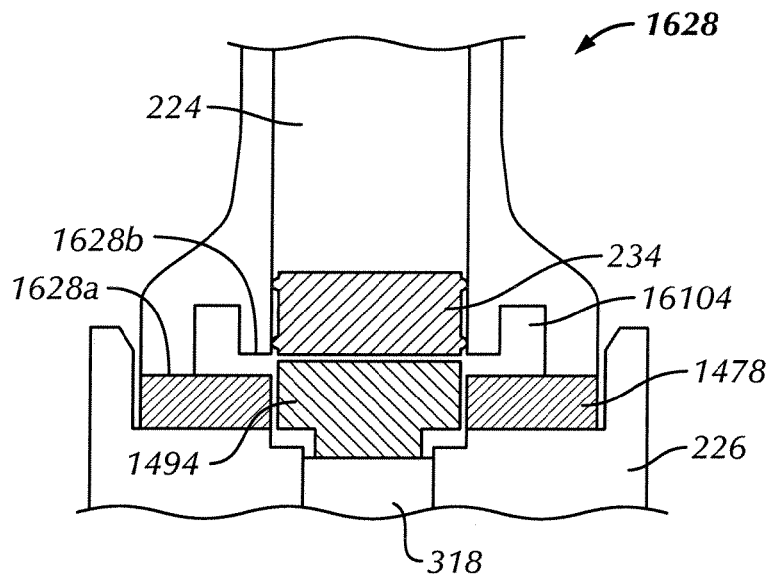
FIG. 16 is a cross sectional view of a cartridge for use with a fluid delivery device similar to the fluid delivery device shown in FIG. 1 in accordance with an exemplary embodiment of the present invention.

Referring to FIG. 16, in one embodiment, a cartridge 1628 may include an overflow channel 16104 to receive displaced hydraulic fluid from pump chamber 318. Once medicinal piston 234 is stopped due to a full fluid reservoir 224 or maxed out relief piston and/or valve 1496, 1598 as described above, cap 1494 may be pushed downwardly toward manifold 226 displacing hydraulic fluid within pump chamber 318 around cap 1494 and into overflow channel 16104. Overflow channel 1494 may be formed by an outer edge 1628a of the proximal end of cartridge 1628 extending axially outwardly further from cartridge 1628 than an inner edge 1628b of the proximal end of cartridge 1628. As cartridge 1628 is brought into contact with seal 1478, outer edge 1628a forms an initial barrier with seal 1478 (shown in FIG. 16). As the seal 1478 is further compressed by outer edge 1628a and medicinal piston 234 pushes on cap 1494, hydraulic fluid is displaced around cap 1494 and into overflow channel 16104 until cartridge 1628 is fully inserted within a fluid delivery device 110. Inner edge 1628a need not necessarily contact seal 1478 upon full insertion of cartridge 1628 but may do so to prevent hydraulic fluid from entering a less than completely full overflow channel 16104 during use. Overflow channel 16104 may be used independently or in combination with any of the features described herein.

Figure 17A:
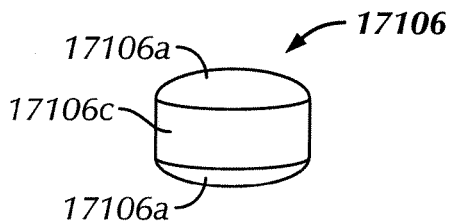
FIG. 17A is a perspective view of a volume displacement cap for use with a fluid delivery device similar to the fluid delivery device shown in FIG. 1 in accordance with an exemplary embodiment of the present invention and shown in an initial position.
Figure 17B:
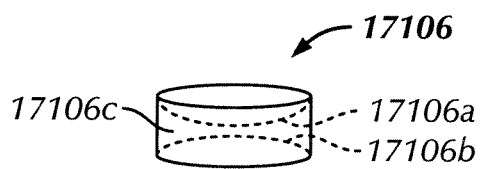
FIG. 17B is a perspective view of the volume displacement cap shown in FIG. 11A in a compressed position.

Referring to FIGS. 17A and 17B, fluid delivery device 110 may include a pop cap 17106. Pop cap 17106 may be used to take in the volume of at least one of fluid reservoir 224 and pump chamber 318 caused by the compression of seal 1478 during insertion of cartridge 1428 into a fluid delivery device 110. Pop cap 17106 may be positioned to abut cap 1494. In one embodiment, cap 1494 includes a recess (not shown) for receiving pop cap 17106. In one embodiment, pop cap 17106 is coupled with cap 1494. In one embodiment, pop cap 17106 is coupled with medicinal piston 234. In one embodiment, pop can 1706 replaces cap 1494.

Pop cap 17106 may be a substantially hollow, enclosed member having a top surface 17106a, a bottom surface 17106b and a sidewall 17106c extending between top and bottom surfaces 17106a, 17106b. Sidewall 17106c may be substantially incompressible in the axial direction in order to avoid adding compressibility to the system during use. In one embodiment, both the top and bottom surfaces are convex in an initial position as shown in FIG. 17A and concave in the compressed position as shown in FIG. 17B. In another embodiment, only one of top and bottom surfaces 17106a, 17106b are moveable between the initial position and the compressed position. In one embodiment, pop cap 17106 is substantially incompressible in the compressed position such that pop cap 17106 absorbs the compression of seal 1478 without substantially impacting fluid reservoir 224 and pump chamber 318. In use, as a cartridge 1428 is inserted into a fluid delivery device 110 and as seal 2478 compresses, bringing the fluid reservoir 224 and pump chamber 318 closer together, this distance is taken up by the change in size of pop cap 17106. In one embodiment, top and bottom surfaces 17106a, 17106b "pop" or snap from the convex or initial position (FIG. 17A) to the concave or compressed position (FIG. 17B). In other embodiment, top and bottom surfaces 17106a, 17106b are more flexible so the transition from the convex or initial position to the concave or compressed position is more gradual. Top and bottom surfaces 17106a, 17106b may be any shape such stepped or initially flat. Pop cap 17106 may be used independently or in combination with any of the other features disclosed herein.

Figure 18:
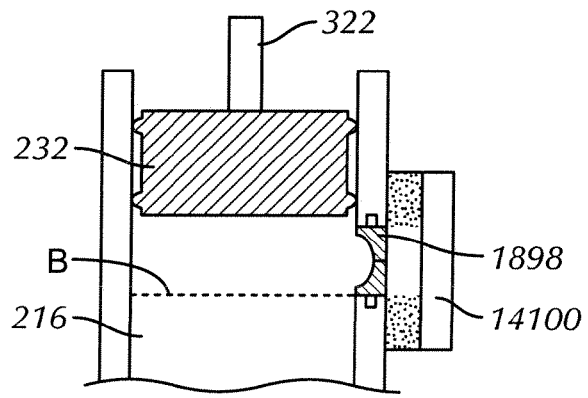
FIG. 18 is a cross sectional view of a bolus relief valve for use with a fluid delivery device similar to the fluid delivery device shown in FIG. 1 in accordance with an exemplary embodiment of the present invention.

Referring to FIG. 18, bolus chamber 216 may include a relief valve 1898 similar to relief valve 1598 described above for cartridge 1428. Relief valve 1898 may be placed downstream of bolus piston 232 such that the hydraulic fluid is expelled from bolus chamber 216 to allow insertion of a cartridge 1428 as medicinal piston 234 is urged against cap 1494 during insertion of cartridge 1428 into a fluid delivery device 110. Relief valve 1898 may include a fluid trap 15100 as described above. In one embodiment, relief valve 1898 is sized and configured such that bolus piston 232 covers relief valve 1898 after deployment of a bolus by bolus actuator 322. An exemplary position of the bottom of bolus piston 232 after delivery of the first bolus is shown by the phantom line B in FIG. 18. Once cartridge 1428 has been inserted into a fluid delivery device 110 and any excess hydraulic fluid has been expelled from pump chamber 318 through relief valve 1898, bolus actuator 322 may move bolus piston 232 to cover relief valve 1898 and fluid delivery device 110 may be used as described above. Relief valve 1898 may be used independently or in combination with any of the features described herein.

Referring to FIG. 19, fluid delivery device 110 may be used with a cartridge 1928 having a displaceable volume. In one embodiment, cartridge 1928 includes a moveable septum 1974. In one embodiment, septum 1974 is displaced by the force exerted on fluid reservoir 224 during insertion of cartridge 1928 into a fluid delivery device 110. In one embodiment, housing 246 or other member fixed relative to manifold 226 may abut septum 1974 once cartridge 1928 has been inserted and septum 1974 has been displaced to prevent further movement of septum 1974.

Referring to FIG. 20, fluid delivery device 110 may be used with a cartridge 2028. Cartridge 2028 may be similar to cartridge 1928 described above with the exception of septum 2074 having a reduced opening 2074b as compared to area 2074a that receives needle 212 during use so that the amount of unused fluid (i.e. fluid remaining within septum 2074 once medicinal piston 234 abuts septum 2074) is reduced. The moveable septums 1974, 2074 may be used independently or in combination with and of the features described herein.

Referring to FIG. 21, in one embodiment, fluid delivery device 110 includes a seal 2178 and piercing member 21108. Piercing member 21108 may extend through seal 2178 upon insertion of cartridge 1428 into a fluid delivery device 110 and compression of seal 2178 creating a fluid passage through seal 2178 such that the hydraulic fluid may pass through seal 2178 and urge medicinal piston 234 through fluid reservoir 224 during use. In one embodiment, seal 2178 includes a center channel or hole 2178b. In one embodiment, seal 2178 includes a pierceable member 2178a. In one embodiment, pierceable member 2178a closes or seals closed hole 2178b. In one embodiment, piercing member 21108 extends from manifold 226 and is in sufficient tolerance with pierceable member 2178a such that pierceable member 2178a is brought into contact with and broken by piercing member 21108 as cartridge 1428 compresses the outer periphery of seal 2178. In one embodiment, piercing member 21108 extends into medicinal piston 234 upon insertion of cartridge 1428 into a fluid delivery device 110 but medicinal piston 234 slides off of piercing member 21108 during fluid delivery. In one embodiment, the hydraulic fluid passes through seal 2178 around piercing member 21108 and through the opening or tear created in pierceable member 2178a. In one embodiment, pierceable member 2178a is a foil. In one embodiment, pierceable member 2178a is a polymeric film.

Figure 22:
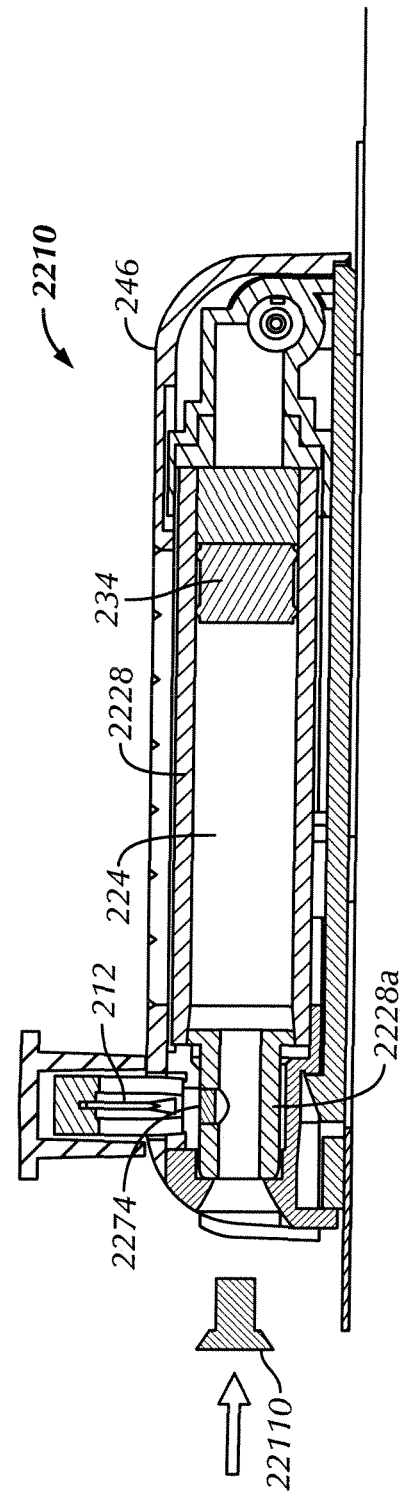
FIG. 22 is a side cross sectional view of a pump chamber and cartridge of a fluid delivery device similar to the fluid delivery device shown in FIG. 1 in accordance with another exemplary embodiment of the present invention.

Referring to FIG. 22, in one embodiment, a fluid delivery device 2210 includes a cartridge 2228. Fluid delivery device 2210 may be similar to embodiments of fluid delivery device 110 described above except that cartridge 2228 may include a stopper 22110 that is inserted after fluid delivery device 2210 is otherwise assembled. Cartridge 2228 may be filled after assembly of fluid delivery device 2210 either by the manufacturer, the end user, or somewhere in between and sealed by stopper 22110. Such an approach could replace the air/liquid venting and displacement configurations described above. In one embodiment, stopper 22110 includes a vent (not shown) to expel any excess air and/or liquid displaced by insertion of stopper 22110 into cartridge 2228.

In one embodiment, cartridge 2228 has a stepped or necked down end 2228a proximate septum 274 to reduce wasted fluid at the end of delivery and to help secure cartridge 2228 to the remainder of fluid delivery device 2210. In one embodiment, septum 274 is integral with stopper 22110 (not shown).

In use, fluid delivery device 2210 may be fully assembled, with the exception of inserting stopper 22110, and then sterilized. The sterilized fluid delivery device 2210 may then be aseptically filled, stopper 22110 inserted into end 2228a to seal cartridge 2228 and the entire fluid delivery device 2210 may then be packaged. Alternatively, following sterilizing, stopper 22110 may be inserted to seal an empty cartridge 2228 and cartridge 2228 is later filled by the user. Stopper 22110 may be pierceable such that a needle of a filling device (not shown) is used to pierce through stopper 22110 and fill fluid reservoir 224.

Figure 23A:
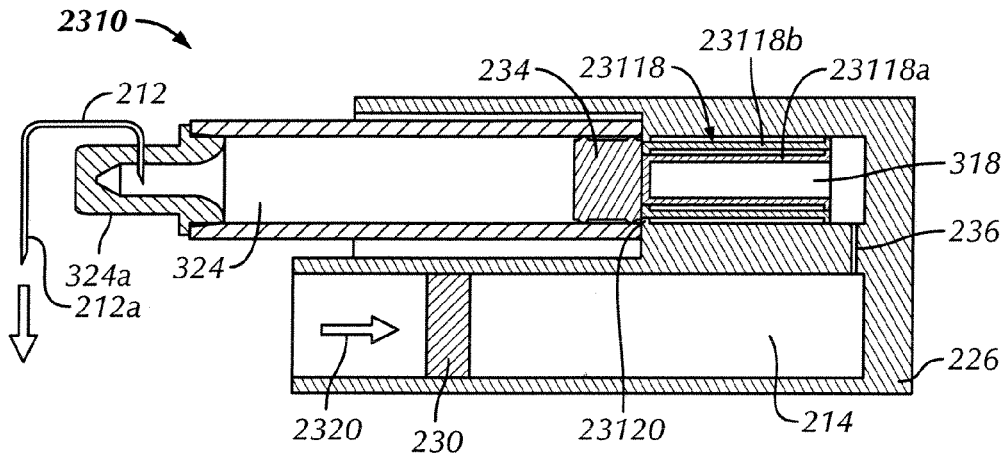
FIGS. 23A-23C are top cross sectional views of a fluid delivery device in accordance with an exemplary embodiment of the present invention having a hydraulic fluid seal shown in the initial, midway and completed positions respectively.
Figure 23B:
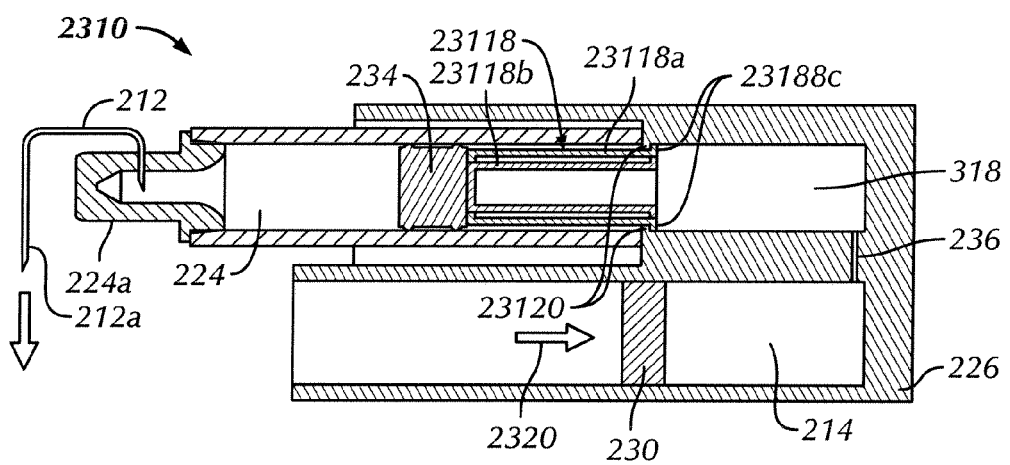
Figure 23C:
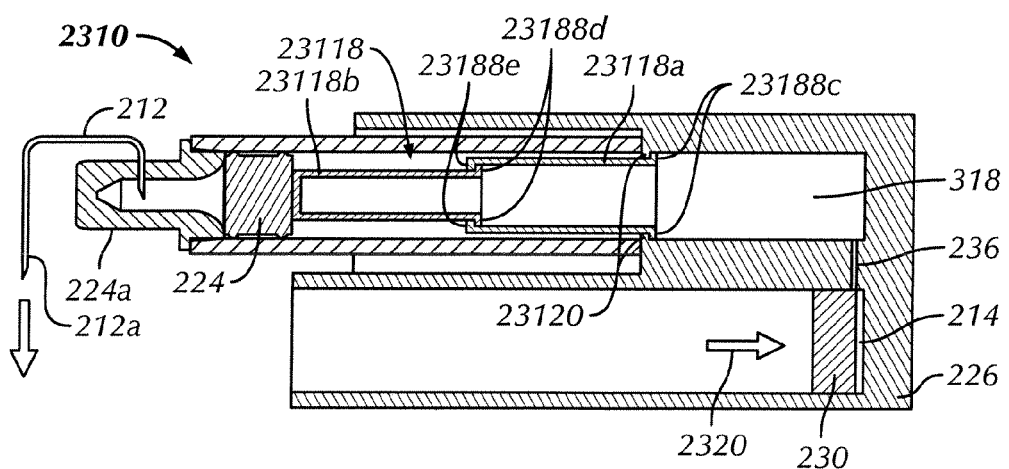

Referring to FIGS. 23A-23C, there is shown a fluid delivery device 2310. Fluid delivery device 2310 is similar to embodiments of fluid delivery device 110 described above with the exception that fluid delivery device 2310 includes a hydraulic fluid seal 23118 that covers and seals the end of hydraulic pump chamber 318. Hydraulic fluid seal 23118 is expandable and is positioned between hydraulic pump chamber 318 and medicinal piston 234. In one embodiment, the proximal end of hydraulic fluid seal 23118 is secured to manifold 226. Hydraulic fluid seal 23118 may be used in combination with the various embodiments of fluid delivery devices 110 described above. In one embodiment, fluid delivery device 2310 is a basal only fluid delivery device as shown. In other embodiments, fluid delivery device 2310 also includes bolus delivery.

In some embodiments, hydraulic fluid seal 23118 is configured to impact the delivery rate profile. In certain embodiments, basal actuator 2320 exerts a pressure on hydraulic basal chamber 214 that decays along the delivery stroke. In one embodiment, the pressure exerted by basal actuator 2320 decays due to the increased length of the hydraulic basal chamber 214. For example, a longer hydraulic basal chamber 214 would require a greater length that basal actuator 2320 must travel. In one embodiment, basal actuator 2320 may be a spring that will have a decreasing force as it expands. In other embodiments, the pressure exerted by basal actuator 2320 decays due to the configurations of basal actuator 2320 (e.g. type of spring, spring travel length), hydraulic basal chamber 214 (e.g. cross sectional size, length) and/or delivery chamber 224 (e.g. cross sectional size, length). The decreasing force exerted by basal actuator 2320 on hydraulic basal chamber 214 over the delivery period, time t, results in a decreased fluid delivery rate R (see FIG. 26A). Though average fluid delivery rate $R_a$ may be achieved, it may be desirable to keep the maximum and minimum delivery rates within a certain absolute value from average fluid delivery rate $R_a$. In one embodiment, hydraulic fluid seal 23118 keeps the variation in the fluid delivery rate closer to average fluid delivery rate $R_a$. In other embodiments it may be desired to fit the delivery profile to a non-constant profile. For example, it may be desirable to have a period of declining delivery followed by a substantially constant delivery at a rate lower than the initial delivery rate.

In one embodiment, the fluid delivery rate may be adjusted by decreasing the moveable cross sectional area of hydraulic fluid seal 23118 as hydraulic fluid seal 23118 expands. In one embodiment, hydraulic fluid seal 23118 includes an inner piston 23118a and an outer piston 23118b. In other embodiments, hydraulic fluid seal 23118 includes additional pistons. In one embodiment, inner piston 23118a is nested within outer piston 23118b such that hydraulic fluid seal 23118 is a telescoping member. In one embodiment, the cross sectional area of inner piston 23118a is less than the cross sectional area of outer piston 23118b. In one embodiment, inner and outer pistons 23118a, 23118b are cylindrically shaped. In other embodiments, inner and outer pistons 23118a, 23118b have any shape that allows an expandable telescoping configuration that reduces in cross sectional area from the proximal end to the distal end such as rectangular or triangular.

Referring to FIG. 23A, in one embodiment, hydraulic fluid seal 23118 is in the collapsed configuration when fluid delivery device 2310 is in the initial position. In the initial position, hydraulic pump chamber 318 has an expandable cross sectional area generally equal to the cross sectional area of hydraulic fluid seal 23118 because both the inner and outer pistons 23118a, 23118b are slideable in the axial direction within hydraulic pump chamber 318 to push against medicinal piston 234. Referring to FIG. 23B, in one embodiment, as medicinal piston 234 advances a length equal to the length of outer piston 23118b, outer piston 23118b is restrained to prevent further axial movement of outer piston 23118b. In one embodiment, outer piston 23118b includes a flange 23118c that extends radially outwardly from the proximal end of outer piston 23118b that engages with a flange 23120 that extends radially inwardly from the distal end of hydraulic pump chamber 318. Once outer piston 23118b is stopped from further axial movement, the moveable cross section of hydraulic pump chamber 318 is reduced to be equal to the cross sectional area of inner piston 23118a. The reduction in the moveable cross sectional area of hydraulic pump chamber 318 increases at time $t_m$ (see FIG. 26B).

In one embodiment, the initial delivery rate using hydraulic fluid seal 23118 is started at a lower rate than if no hydraulic fluid seal 23118 were used (compare FIGS. 26A and 26B). As described above, the initial delivery rate may be controlled by the configuration of flow restrictor 236. In one embodiment, the cross sectional area of inner piston 23118a is approximately half the cross sectional area of outer piston 23118b and inner piston 23118a while nested together resulting in delivery rate at time $t_m$ increasing to approximately the initial delivery rate. In such an embodiment, reducing the cross sectional area by half would require the pressure in hydraulic basal chamber 214 to double in order to maintain the same force in hydraulic pump chamber 318 against medicinal piston 234. The increase in the pressure in hydraulic basal chamber 214 will therefore slow the flow rate through flow restrictor 236 by less than half the prior rate while the oil volume to displace inner piston 23118a is reduced to half the oil volume to displace both inner and outer pistons 23118a, 23118b (See FIG. 26B). The net result is that the velocity of the inner piston 23118a and the medicinal piston 234 increases to a new rate.

In other embodiments, the change in cross sectional area of hydraulic fluid seal 23118 is a suitable ratio to provide the desired change in delivery rate and/or to accommodate additional pistons. In one embodiment, inner piston 23118a includes a flange 23188d that extends radially outwardly from the proximal end of inner piston 23118a that engages with a flange 23118e that extends radially inwardly from the distal end of outer piston 23118b. In one embodiment, flanges 23188c, 23120, 23188d, 23188e are also used to direct the movement of the inner and outer pistons 23118a, 23118b and seal the hydraulic fluid off from the outside of hydraulic fluid seal 23118.

Figure 24A:
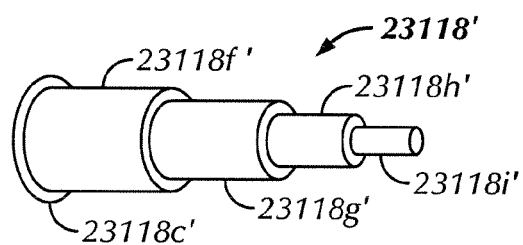
FIG. 24A is a perspective view of another exemplary embodiment of the hydraulic fluid seal in the expanded configuration.
Figure 24B:
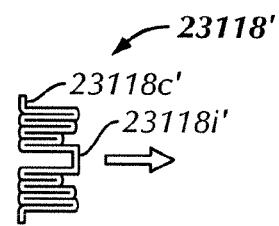
FIG. 24B is a cross sectional view of the hydraulic fluid seal of FIG. 24A shown in the initial configuration.

Referring to FIGS. 24A-25B, there are shown second and third exemplary embodiments 23118', 23118" of hydraulic fluid seal 23118. In one embodiment, hydraulic fluid seal 23118' includes two or more connected sections (e.g., sections 23118f-23118i') rather than two or more slideable pistons. In one embodiment, hydraulic fluid seal 23118' is comprised of a flexible and substantially inelastic membrane such that the sections of the hydraulic fluid seal 23118' may be folded in the collapsed configuration (FIG. 24B) and rolled out to the extended configuration (FIG. 24A). In other embodiments, hydraulic fluid seal 23118' is comprised of a stretchable or elastic material such that the changes in the stretching force is used to control the fluid delivery rate instead of or in combination of the rolled out reduced cross sectional area of hydraulic fluid seal 23118'. In one embodiment, flange 23118c', 23118c" is attached to hydraulic pump chamber 318 and the distal end extends distally during use to urge medicinal piston 234.

Figure 25A:
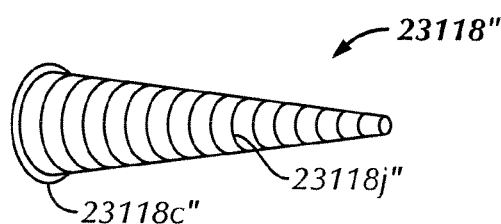
FIG. 25A is a perspective view of another exemplary embodiment of the hydraulic fluid seal in the expanded configuration.
Figure 25B:
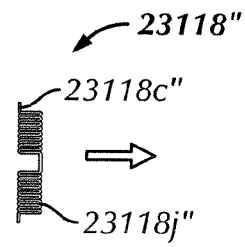
FIG. 25B is a cross sectional view of the hydraulic fluid seal of FIG. 25A shown in the initial configuration.

In one embodiment, increasing the number of sections 23118f-23118i' of hydraulic fluid seal 23118' brings the maximum and minimum delivery rate closer to average delivery rate $R_a$ (see FIG. 26C). In one embodiment, hydraulic fluid seal 23118" has a conical rather than stepped shape so that the 'saw tooth' delivery rate of FIG. 26C is smoothed out even further. In one embodiment, the contour of hydraulic fluid seal 23118" is shaped to closely counter the decrease in the force from basal actuator 2320. Referring to FIGS. 25A and 25B, in one embodiment, hydraulic fluid seal 23118" has a generally constant decreasing cross sectional area toward its distal end. In other embodiments, hydraulic fluid seal 23118" has a cross sectional area that decreases at by an increasing (convex outer profile) or decreasing rate (concave outer profile) or some combination of no reduction and constant, decreasing, increasing or decreasing rates to control or program the fluid delivery rate to match a desired delivery profile. In one embodiment, the stepped configuration helps to ensure that hydraulic fluid seal 23118' is properly and consistently folded. In one embodiment, hydraulic fluid seal 23118' or hydraulic fluid seal 23118" includes fold lines or grooves, 23118j" that help to dictate where the folds in hydraulic fluid seal 23118', 23118" occur.

Referring to FIGS. 27A-27C, there is shown a fourth exemplary embodiment 23118'" of hydraulic fluid seal 23118. In one embodiment, hydraulic fluid seal 23118'" includes a plurality of fold lines or pleats 23118b'" that allow hydraulic fluid seal 23118'" to compress in the initial position (FIG. 27A) and expand to the expanded configuration (FIG. 27C). In one embodiment, the cross sectional area of hydraulic fluid seal 23118'" remains generally constant. In such an embodiment, hydraulic fluid seal 23118'" is attached to manifold 226 to seal hydraulic pump chamber 318 and hydraulic fluid seal 23118'" is not configured to impact the delivery fluid rate.

It will be appreciated by those skilled in the art that changes could be made to the exemplary embodiments shown and the embodiments described above without departing from the broad inventive concept thereof. It should be understood that the individual embodiments described herein are meant to be freely combined with one another, such that any particular combination may simultaneously contain two or more features described in different embodiments whenever appropriate. In addition, all embodiments described for one aspect of the invention (such as a device) also applies to other aspects of the invention (e.g., method or system) whenever appropriate. The order in which the steps of described methods are performed is purely illustrative in nature, and may not need to be performed in the exact sequence they are described. In fact, the steps can be performed in any suitable order or in parallel, unless otherwise indicated as inappropriate by the present disclosure or in context. Unless specifically set forth herein, the terms "a", "an" and "the" are not limited to one element but instead should be read as meaning "at least one".

We claim:

1. A fluid delivery device comprising:
   a housing having a first hydraulic chamber and a second hydraulic chamber;
   a flow restrictor fluidly coupling the first hydraulic chamber and the second hydraulic chamber;
   a cartridge having a container forming a fluid reservoir sealed at a proximal end with a piston, the cartridge being insertable into the housing to couple the piston with the second hydraulic chamber, the fluid reservoir being substantially filled with a liquid and the second hydraulic chamber being filled with a hydraulic fluid prior to inserting the cartridge within the housing, the cartridge including a septum configured to be pierced by a delivery needle; and
   an actuator coupled to the housing and configured to deliver a force to the piston through the first and second hydraulic chambers.

2. The fluid delivery device of claim 1, further comprising a cartridge seal coupled between the proximal end of the cartridge and the housing when the cartridge is inserted into the housing.

3. The fluid delivery device of claim 2, wherein the cartridge seal is compressible.

4. The fluid delivery device of claim 2 further comprising:
   a hydraulic cap covering an end of the second hydraulic chamber, the hydraulic cap extending through the cartridge seal and coupling the piston and the second hydraulic chamber.

5. The fluid delivery device of claim 4, wherein the hydraulic cap is substantially rigid.

6. The fluid delivery device of claim 2, wherein the proximal end of the cartridge includes an overflow channel in fluid communication with the second hydraulic chamber when the cartridge is inserted into the housing.

7. The fluid delivery device of claim 6, wherein the overflow channel is formed between an outer peripheral edge of the proximal end of the cartridge and an inner peripheral edge of the proximal end of the cartridge, the outer peripheral edge extending axially further from the cartridge than the inner peripheral edge.

8. The fluid delivery device of claim 2, wherein the cartridge seal covers an end of the second hydraulic reservoir prior to inserting the cartridge into the housing and the cartridge seal is pierced upon insertion of the cartridge into the housing.

9. The fluid delivery device of claim 8, wherein the second hydraulic reservoir includes a piercing member configured to pierce the cartridge seal upon insertion of the cartridge into the housing.

10. The fluid delivery device of claim 9, wherein the piercing member includes a needle.

11. The fluid delivery device of claim 1, wherein the septum is slideably coupled with the container.

12. The fluid delivery device of claim 11, wherein the septum is configured to slide distally with respect to the container upon inserting the cartridge into the housing.

13. The cartridge of claim 11, wherein the septum includes a space for receiving an end of the delivery needle and a fluid passageway fluidly coupling the space and the fluid reservoir, the fluid passageway having a cross sectional area that is less than a cross sectional area of the space.

14. The cartridge of claim 11, wherein the septum seals a distal end of the container.

15. The cartridge of claim 11, wherein the septum is displaced with respect to the container when the septum is displaced upon inserting the cartridge into the housing.

16. The fluid delivery device of claim 1, wherein the second hydraulic chamber is configured to expel hydraulic fluid upon insertion of the cartridge into the housing.

17. The fluid delivery device of claim 1, wherein the cartridge further comprises a relief valve, the piston configured to expel air and/or fluid through the relief valve upon insertion of the cartridge into the housing.

18. The fluid delivery device of claim 1, wherein the cartridge further comprises a relief piston configured to slide distally upon insertion of the cartridge into the housing.

19. The fluid delivery device of claim 1 further comprising:
   a cap coupling the piston and the second hydraulic reservoir when the cartridge is inserted into the housing, the cap having a side wall and at least one of a top surface or a bottom surface that extends axially outwardly from the side wall, at least one of the top surface or the bottom surface being configured to invert upon inserting the cartridge into the housing.

20. The fluid delivery device of claim 1, wherein the cartridge includes a volume and a pressure, the volume being reduceable to enable insertion of the cartridge into the housing prior to engagement with the delivery needle and without changing the pressure.

21. The fluid delivery device of claim 1, wherein the cartridge includes an pre-insertion pressure prior to inserting the cartridge into the housing and an assembled pressure after the cartridge has been inserted into the housing and prior to engagement with the delivery needle, the pre-insertion pressure being generally equal to the assembled pressure.

22. The fluid delivery device of claim 1, wherein there is substantially no air between the second hydraulic chamber and the septum after the cartridge has been inserted into the housing.

23. A fluid delivery device comprising:
   a housing having a first hydraulic chamber and a second hydraulic chamber;
   a flow restrictor fluidly coupling the first hydraulic chamber and a second hydraulic chamber;
   a cartridge forming a fluid reservoir between a slideable piston and a septum configured to receive a delivery needle, the cartridge including a stopper configured to seal a distal end of the cartridge after the fluid reservoir is substantially filled with a liquid, the piston being coupled with the second hydraulic chamber; and an actuator coupled to the housing and configured to deliver a force to the piston through the first and second hydraulic chambers.

24. The fluid delivery device of claim 23, wherein the delivery needle is configured to pierce the septum in a direction generally perpendicular to a direction the stopper is inserted in the distal end of the cartridge.

25. A fluid delivery device comprising:
a housing having a first hydraulic chamber and a second hydraulic chamber;
a flow restrictor fluidly coupling the first hydraulic chamber and a second hydraulic chamber;
a fluid reservoir having a piston;
a seal sealing an end of the second hydraulic chamber and configured to couple with the piston, the seal being expandable between a compressed position and an expanded position; and
an actuator coupled to the first hydraulic chamber and configured to expand the seal, move the piston and deliver a force to the fluid reservoir through the first and second hydraulic chambers.

26. The fluid delivery device of claim 25, wherein the cross sectional area of a distal end of the seal is smaller than the cross sectional area of a proximal end of the seal in the expanded position.

27. The fluid delivery device of claim 26, wherein the seal includes at least two telescoping members.

28. The fluid delivery device of claim 26, wherein the seal includes at least two cylindrical members having different diameters.

29. The fluid delivery device of claim 26, wherein the seal is generally conically shaped in the expanded position.

30. The fluid delivery device of claim 25, wherein the fluid reservoir is a prefilled cylindrical cartridge that is insertable into the housing.

* * * * *